United States Patent
Bajaj et al.

(10) Patent No.: US 11,253,554 B2
(45) Date of Patent: Feb. 22, 2022

(54) BACTERIAL PROFILE TO DETECT FUNGAL TAXA ABUNDANCE IN THE GUT

(71) Applicants: Virginia Commonwealth University, Richmond, VA (US); George Mason University, Fairfax, VA (US)

(72) Inventors: Jasmohan Bajaj, Richmond, VA (US); Patrick M. Gillevet, Manassas, VA (US)

(73) Assignees: Virginia Commonwealth University, Richmond, VA (US); George Mason University, Fairfax, VA (US)

( * ) Notice: Subject to any disclaimer, the term of this patent is extended or adjusted under 35 U.S.C. 154(b) by 378 days.

(21) Appl. No.: 16/339,192

(22) PCT Filed: Oct. 5, 2017

(86) PCT No.: PCT/US2017/055440
§ 371 (c)(1),
(2) Date: Apr. 3, 2019

(87) PCT Pub. No.: WO2018/067887
PCT Pub. Date: Apr. 12, 2018

(65) Prior Publication Data
US 2019/0224252 A1    Jul. 25, 2019

Related U.S. Application Data

(60) Provisional application No. 62/404,488, filed on Oct. 5, 2016.

(51) Int. Cl.
*C12Q 1/04* (2006.01)
*A61K 35/741* (2015.01)
(Continued)

(52) U.S. Cl.
CPC .............. *A61K 35/741* (2013.01); *A61P 1/16* (2018.01); *A61P 31/10* (2018.01); *C12N 1/14* (2013.01);
(Continued)

(58) Field of Classification Search
CPC .......... A61K 35/741; A61P 1/16; A61P 31/10; C12N 1/14; C12N 1/20; C12Q 1/04;
(Continued)

(56) References Cited

U.S. PATENT DOCUMENTS

2014/0179726 A1    6/2014  Bajaj et al.

OTHER PUBLICATIONS

Iryna Gavrysh, The Ways of Optimizing Treatment the Patients with Liver Cirrhosis, 2013, The Pharma Innovation—Journal, vol. 2, No. 5, pp. 86-90 (Year: 2013).*

(Continued)

*Primary Examiner* — David W Berke-Schlessel
*Assistant Examiner* — Trent R Clarke
(74) *Attorney, Agent, or Firm* — Thomas | Horstemeyer, LLP

(57) ABSTRACT

Disclosed herein are compositions and methods for diagnosing fungal dysbiosis in the gut of a subject with cirrhosis that involves assaying a sample from the subject for bacterial taxa. These compositions and methods are based on the discovery that there is significant correlation between fungal and bacterial diversity in gut microbiota of cirrhotic patients. Therefore, disclosed herein is a method for treating a subject with liver cirrhosis that involves assaying a gut sample from the subject for bacterial taxa to generate a bacterial profile, comparing the bacterial profile to control profiles to predict fungal dysbiosis; and treating the subject for fungal dysbiosis.

8 Claims, 19 Drawing Sheets

Specification includes a Sequence Listing.

(51) Int. Cl.
  *C12Q 1/6883* (2018.01)
  *C12Q 1/689* (2018.01)
  *A61P 1/16* (2006.01)
  *A61P 31/10* (2006.01)
  *C12N 1/14* (2006.01)
  *C12N 1/20* (2006.01)

(52) U.S. Cl.
  CPC ............... *C12N 1/20* (2013.01); *C12Q 1/04* (2013.01); *C12Q 1/689* (2013.01); *C12Q 1/6883* (2013.01)

(58) Field of Classification Search
  CPC ........ C12Q 1/18; C12Q 1/686; C12Q 1/6806; C12Q 1/689
  See application file for complete search history.

(56) References Cited

OTHER PUBLICATIONS

Jerry W. Pickering, Howard W. Sant, Catherine A. P. Bowles, William L. Roberts and Gail L. Woods, Evaluation of a (1→3)-β-D-Glucan Assay for Diagnosis of Invasive Fungal Infections, 2005, J. Clin. Microbiol., vol. 43, No. 12, p. 5957-5962 (Year: 2005).*
International Search Report issued for PCT/US2017/055440, dated Dec. 26, 2017.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
agagtttgat cctggctcag                                               20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
gctgcctccc gtaggagt                                                 18
```

```
<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
cttggtcatt tagaggaagt aa                                              22

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gctgcgttct tcatcgatgc                                                 20
```

BACTERIAL PROFILE TO DETECT FUNGAL TAXA ABUNDANCE IN THE GUT

CROSS-REFERENCE TO RELATED APPLICATIONS

This application claims benefit of U.S. Provisional Application No. 62/404,488, filed Oct. 5, 2016, which is hereby incorporated herein by reference in its entirety.

BACKGROUND

Liver cirrhosis is a major cause of death and disability worldwide. One of the major reasons for this mortality is related to infections that often stem from the gut. Gut bacterial dysbiosis in cirrhosis has been associated with these infections, which can lead to organ failure and death. With the rampant overuse of antibiotics in cirrhosis, culture-negative and fungal infections are being increasingly recognized. However, the effect of antibiotic use and culture-negative infections on the gut fungal mycobiome is unclear. Cirrhotic patients have a high likelihood of developing infections because of altered immune response, multiple hospitalizations and instrumentations and the overuse of antibiotics for treatment and prophylaxis of infections. While most infections are presumed to be bacterial, recent studies have noted a significant increase in documented fungal infections or infections in which there is no growth i.e. culture-negative infections. However, it is experimentally difficult to detect the fungal component in fecal and oral samples because of low absolute abundance with respect to the bacterial mass and the difficulty in obtaining efficient DNA extraction for fungal cells.

SUMMARY

Disclosed herein are compositions and methods for diagnosing fungal dysbiosis in the gut of a subject with cirrhosis that involves assaying a sample from the subject for bacterial taxa. These compositions and methods are based on the discovery that there is significant correlation between fungal and bacterial diversity in gut microbiota of cirrhotic patients.

Therefore, disclosed herein is a method for treating a subject with liver cirrhosis that involves assaying a gut sample from the subject for bacterial taxa to generate a bacterial profile, comparing the bacterial profile to control profiles to predict fungal dysbiosis; and treating the subject for fungal dysbiosis.

The disclosed method has several advantages. In some cases, the sample from the subject can be culture-negative for fungal infection but the method is able to predict fungal taxa abundance based on bacterial dysbiosis.

In some embodiments, the gut sample comprises DNA from a biological tissue or fluid, such as stool, rectal swab, mucosal biopsy, skin, saliva, or oral swab.

The sample can be assayed using known methods, such as nucleic acid detection techniques using bacteria-specific primers or probes. For example, the assay can involve PCR amplification of the DNA with bacterial specific primers for variable regions of the 16S rRNA gene. In particular embodiments, these primers can be fusion primers that contain a sample barcode and appropriate adapters for the Nextgen Sequencing. This allows for pooling of samples and sequencing of a NextGen sequencer, followed by demultiplexing based on the sample barcodes. From the sequences, the relative abundance of bacterial taxa can be determined and compared to abundance tables from control samples, some of which had been shown to be associated with fungal dysbiosis. This allows for prediction of fungal dysbiosis in the subject based on the bacterial taxa. In particular embodiments, the bacterial profile associated with fungal dysbiosis comprises a reduction in bacterial diversity.

The predicted fungal dysbiosis can in some embodiments be an indication of fungal overgrowth. In these embodiments, the subject can be treated with anti-fungal therapy instead of, or in addition to, antibiotic therapy.

In some embodiments, the fungal dysbiosis is an indication of excessive antibiotic use. In these embodiments, the subject can be treated by ceasing or reducing antibiotic therapy.

In some embodiments, the fungal dysbiosis is an indication of microbiome depletion. In these embodiments, the subject can be treated with probiotics, prebiotics, or fecal microbial transplant.

The bacteria taxa assayed in the disclosed methods can in some embodiments be selected from the group consisting of *Collinsella, Enterococcus, Streptococcus, Coprococcus, Fusicatenibacter, Lachnospiraceae* incertae sedis, *Roseburia, Ruminococcus2, Anaerostipes, Fusicatenibacter, Lachnobacterium, Robinsoniella, Ruminococcus, Anaerotruncus, Hydrogenoanaerobacterium*, and *Megasphaera*.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
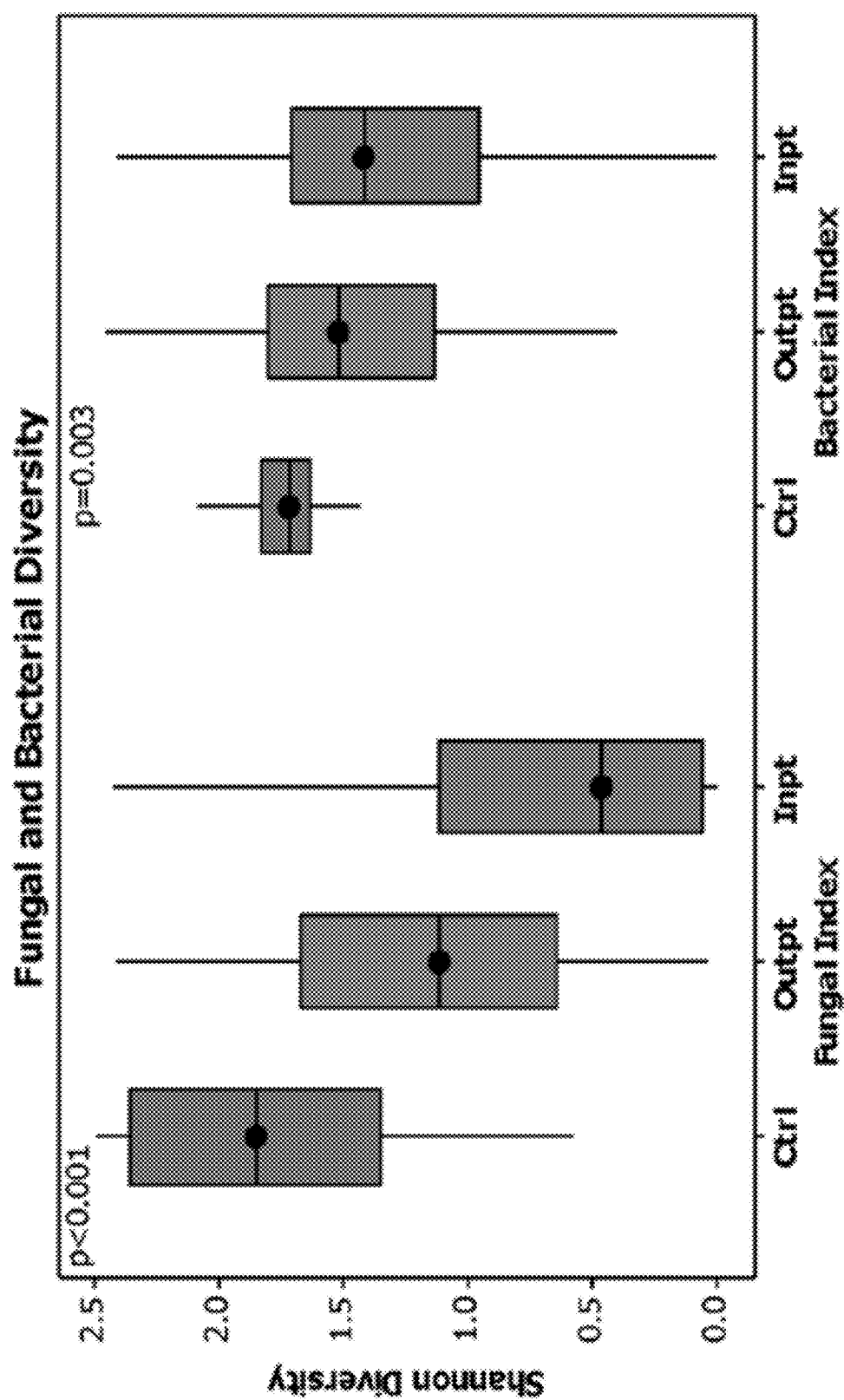
FIG. 1. Cross-sectional study diversity. (A) Shannon diversity in fungal and bacterial taxa was the highest in healthy controls and significantly lowest in inpatients. Data are presented as median and 95% CI with p values based on Kruskal-Wallis test. Ctrl, controls; Inpt, inpatients with cirrhosis; outpt, outpatients with cirrhosis. (B) Fungal diversity was significantly correlated with bacterial diversity. Black circles, infected patients with cirrhosis; red squares, uninfected patients with cirrhosis; green diamonds, healthy controls. (C) Shannon diversity indices for both fungi and bacteria were the highest in healthy controls and lowest in inpatients. Data are presented as median and 95% CI with p-values based on Kruskal-Wallis test. Ctr, controls; Cirr, outpatients with cirrhosis not on rifaximin, lactulose or SBP prophylaxis; Cneg, culture-negative infections; Cpos, culture-positive infections; Lac, outpatients with cirrhosis on lactulose; R+SB, outpatients with cirrhosis on rifaximin and/or SBP prophylaxis; Uninf, uninfected inpatients with cirrhosis.

Disclosed herein is a method for treating a subject with liver cirrhosis that involves assaying a gut sample from the subject for bacterial taxa to generate a bacterial profile, comparing the bacterial profile to control profiles to predict fungal dysbiosis; and treating the subject for fungal dysbiosis.

In some embodiments, the gut sample comprises DNA from a biological tissue or fluid, such as stool, rectal swab, mucosal biopsy, skin, saliva, or oral swab.

The sample can be assayed using known methods, such as nucleic acid detection techniques using bacteria-specific primers or probes. For example, the assay can involve PCR amplification of the DNA with bacterial specific primers for variable regions of the 16S rRNA gene. In particular embodiments, these primers can be fusion primers that contain a sample barcode and appropriate adapters for the Nextgen Sequencing. This allows for pooling of samples and sequencing of a NextGen sequencer, followed by demultiplexing based on the sample barcodes. From the sequences, the relative abundance of bacterial taxa can be determined and compared to abundance tables from control samples, some of which had been shown to be associated with fungal dysbiosis. This allows for prediction of fungal dysbiosis in the subject based on the bacterial taxa. In particular embodiments, the bacterial profile associated with fungal dysbiosis comprises a reduction in bacterial diversity.

Abundance tables from control values can be determined in some embodiments using the following method.

DNA extraction from biological samples of healthy and cirrhotic subjects with and without fungal infections. The DNA can be preserved, for example, in RNA-Later. The DNA sample can be amplified by PCR with bacterial specific primers for variable regions of the 16S rRNA gene and with fungal specific primers for the ITS gene. For example, these primers can be fusion primers that contain a sample barcode and appropriate adapters for the Nextgen Sequencing. Multiple samples can be pooled and sequenced on a NextGen sequencer, e.g. using an Illumina or Ion Torrent technology. The resulting data from the NextGen sequencing can be demultiplexed based on the sample barcodes and reads associate with the samples. The reads can then assigned a bacterial taxonomic identification and a fungal taxonomic identification based on, for example, the RDP11 Bayesian classifier. Relative abundance tables can then generated for each patient based on the taxonomic identification and the number of reads per sample. The abundance tables can then be classified based on clinical metadata. Statistical analysis can then be used to identify bacterial and fungal taxa profiles that are associated with each clinical class.

Finally, based on the disclosed associations between bacterial and fungal diversity, non-parametric statistical analysis can be used to associate bacterial taxa with fungal taxa for each of the clinical classes. Examples of non-parametric statistical analysis include Metastats, LEFSE, Kruskal Wallisace, and UNIFRAC. Machine learning can be used to validate the statistical associations between fungal and bacterial taxa and clinical classes.

The disclosed method can therefore involve assaying for bacterial taxa alone, and using the produced control tables to predict fungal taxa from the bacterial taxa values. For example, a physician can have bacterial 16S rDNA analysis done on a patient microbiome sample and from that predict (1) which patients have fungal overgrowth requiring a lower threshold for anti-fungal coverage, (2) which patients are unlikely to sustain further antibiotic use, (3) which patients may need repletion of their microbiome by beneficial bacteria using probiotics, prebiotics or fecal microbial transplant, and (4) which patients may get re-hospitalized within 90 days which patients to treat with antibiotic and which patients to treat with antifungal agents.

The predicted fungal dysbiosis can in some embodiments be an indication of fungal overgrowth. In these embodiments, the subject can be treated with anti-fungal therapy instead of, or in addition to, antibiotic therapy.

In some embodiments, the fungal dysbiosis is an indication of excessive antibiotic use. In these embodiments, the subject can be treated by ceasing or reducing antibiotic therapy.

In some embodiments, the fungal dysbiosis is an indication of microbiome depletion. In these embodiments, the subject can be treated with probiotics, prebiotics, or fecal microbial transplant.

The bacteria taxa assayed in the disclosed methods can in some embodiments be selected from the group consisting of *Collinsella, Enterococcus, Streptococcus, Coprococcus, Fusicatenibacter, Lachnospiraceae* incertae sedis, *Roseburia, Ruminococcus2, Anaerostipes, Fusicatenibacter, Lachnobacterium, Robinsoniella, Ruminococcus, Anaerotruncus, Hydrogenoanaerobacterium,* and *Megasphaera.*

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "reduce" refers to lowering by, for example, 5%, 10%, 20%, 30%, 40%, 50%, 60%, 70%, 80%, 90%, or 99% when compared to a positive control.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Methods

A cross-sectional and three longitudinal studies were performed. The protocols were approved by IRBs at the VCU and Richmond Va. Medical Centers, and all subjects gave written informed consent for the study:

Cross-Sectional Study

Healthy controls that were age-matched were enrolled with two sets of patients with cirrhosis, outpatients and inpatients. Healthy controls were outpatients without any chronic diseases or medications. Patients with cirrhosis were included who were diagnosed using liver biopsy, evidence of frank decompensation or radiological features of cirrhosis who were between 21 and 75 years. Patients who were unable to give consent or provide stool within 48 hours of admission, with alcohol misuse, alcoholic hepatitis, on antifungal medications and with gastrointestinal bleeding episodes within 6 weeks were excluded. Also excluded were those undergoing HCV eradication or those on probiotics within the last 3 months. These eligibility criteria for cirrhosis and healthy controls were used for all cross-sectional and longitudinal studies.

All patients had medications and diabetes status recorded. Blood was drawn for endotoxin assay (Limulus amebocyte lysate assay) and stool collected for microbiota analysis.

Outpatients with cirrhosis were recruited from the clinics after informed consent. Inpatients with cirrhosis consisted of three groups: (1) uninfected, (2) culture-negative and (3) culture-positive infections. For the culture-negative group, we included all infected patients whose routine bacterial and fungal cultures were negative for any organism but had signs of infection. These included >250 polymorphonuclear cells on ascites fluid with negative culture for SBP, specific radiological features of pneumonia without positive sputum or blood culture and so on (Bajaj J S, et al. Hepatology 2012 56:2328-35). All these had received at least one dose of antibiotics per standard of care before stool collection. The patients with culture-positive infections had one or more bacterial or fungal organisms isolated as the cause. However, the stool collection had taken place before that determination was made. In the uninfected group, the included patients fit the same criteria for hospitalization without an infection either suspected or documented and without current absorbable antibiotic use for presumed infections.

All patients were followed up for 90 days or until death or liver transplant. Non-elective hospitalizations 90 days pos-tenrolment were studied. Clinical and microbiota (fungal and bacterial) parameters were compared. A multivariable backwards logistic regression model was created by including clinical and microbiota (fungal and bacterial) variables that were p<0.10 on univariate analysis with 90-day hospitalization as the outcome.

Longitudinal Studies

Outpatients with cirrhosis who gave stool samples at least 6 months apart with stability of the cirrhosis course between visits were enrolled.

The impact of PPI on fungal parameters were analyzed from a prior trial in which 40 mg of omeprazole was administered daily for 14 days in compensated outpatients with cirrhosis and healthy controls, (Bajaj J S, et al. Am J Physiol Gastrointest Liver Physiol 2014 307:G951-G957).

Antibiotics Compared with Standard of Care:

A cohort of outpatients with prior hepatic encephalopathy on lactulose and rifaximin were recruited after written informed consent and were randomised into two groups using a random number generator; one group was administered 5 days of broad-spectrum antibiotics (metronidazole 500 mg three times a day, ciprofloxacin 500 mg twice a day and amoxicillin 500 mg twice a day), while the other group was followed without intervention for the same duration. Stool samples were collected at baseline and at day 5.

For all these studies, Shannon diversity indices for both bacterial and fungal taxa as well as LEFSe comparisons (Segata N, et al. Genome Biol 2011 12:R60) at baseline and the end of study were performed and compared.

Detailed Microbial and Bioinformatics Methods

Microbial DNA were isolated from stool samples as previously described (Gillevet P, et al. Chem Biodivers 2010 7:1065-75). 16S rRNA Bacterial community analysis: The V1 and V2 hyper-variable regions of the bacterial 16S ribosomal RNA (rRNA) gene were sequenced on a PGM Ion Torrent Next-generation sequencer using Multitag fusion primers targeting the V1-V2 region (27F: 5'-AGAGTTT-GATCCTGGCTCAG-3' (SEQ ID NO:1), 355R: 5'-GCTGCCTCCCGTAGGAGT-3' (SEQ ID NO:2)). Amplicons for 96 samples were then sequenced together to generate >20,000×400 base reads per sample.

Quality Control:

A negative control (water) and a known positive control were used in each batch of microbial DNA sequencing to assess laboratory variability and contamination (Sikaroodi M, et al. Biotechniques 2012 53:381-3).

Fungal Community Analysis:

Similarly, the ITS1 regions of the fungal 18S ribosomal RNA (rRNA) gene were sequenced on a PGM Ion Torrent Next-generation sequencer using Multitag fusion primers (ITS1F: 5'-CTTGGTCATTTAGAGGAAGTAA-3' (SEQ ID NO:3); ITS2: 5'-GCTGCGTTCTTCATCGATGC-3' (SEQ ID NO:4)). Amplicons for 96 samples were sequenced together to generate >10,000×400 base reads per sample.

Figure 6:
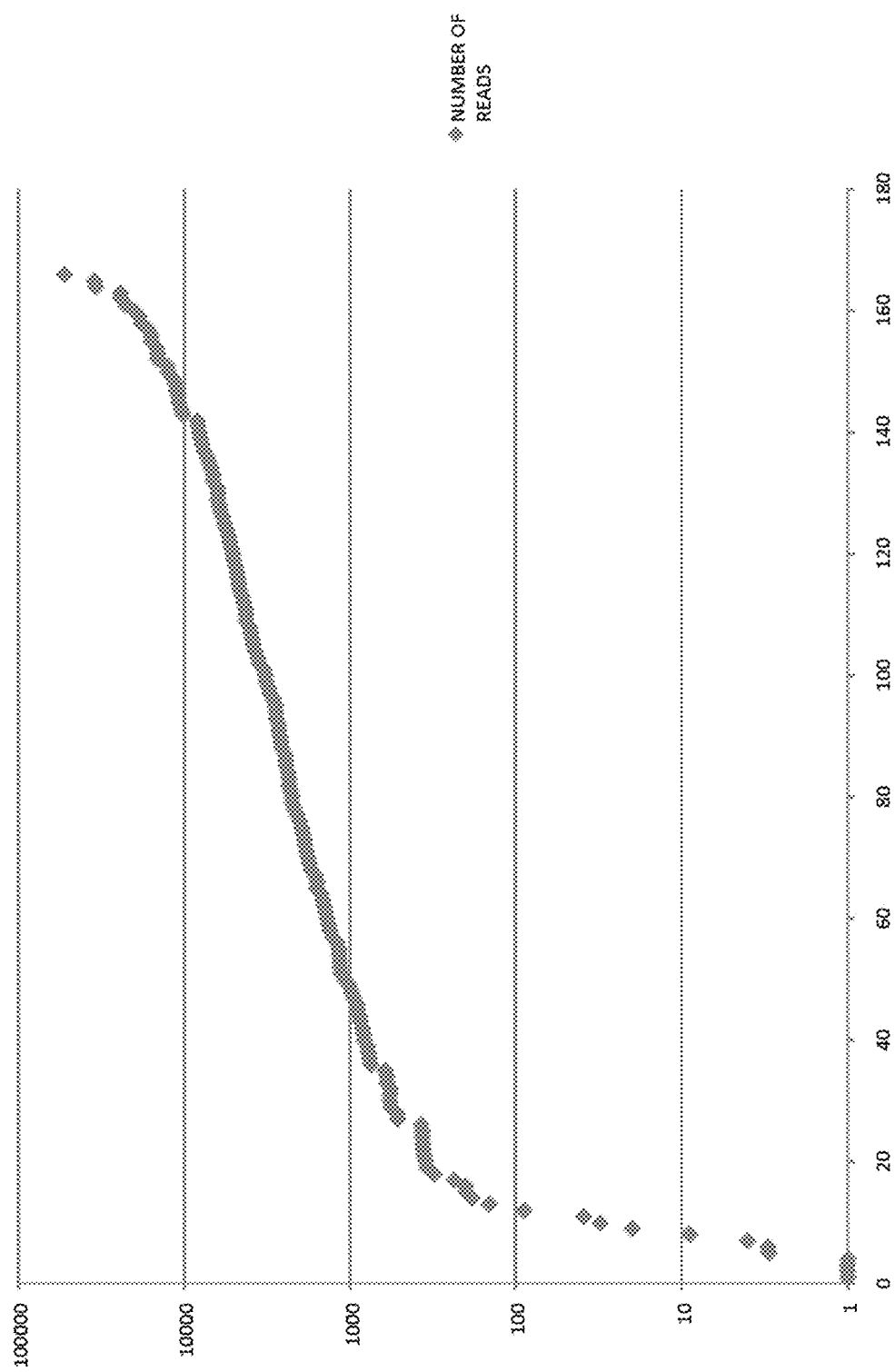
FIG. 6. Graph showing number of reads per sample for PCR products.

The mycobiome is generally less diverse than the microbiome and thus required fewer reads to interrogate this community (Ghannoum M A, et al. PLoS pathogens 2010 6:e1000713). Greater than 1000 reads for bacteria and greater than 100 reads for fungi were used given the relatively lower abundance of fungal taxa as the lowest number chosen to be acceptable. Fungal primers produced strong PCR product for about 73% of the samples while the rest either did not produce any product or the products were very weak. All the samples were repeated with bacterial primers and essentially all samples produced strong PCR products which indicated that the DNA was good quality and was not degraded. Due to the dramatic difference in product intensity it was harder to normalize the barcoded products for pooling which resulted in a wide range for read numbers for the fungal samples. A cutoff of 100 reads per sample was used as that was clearly above the negative control and is the break point in FIG. 6.

This was a conservative approach to avoid subjectively biasing the results. It should be noted that if noise was introduced into the analysis by the samples with low reads, it would have made the LEFSE analysis less sensitive and would have exclude more taxa in from the results. Also the results that were found are biologically plausible and change with the underlying cirrhosis and antibiotic use severity. This low-read phenomenon is the result of two issues, first that the mycobiome is rarer than bacteria and, second, that the genome size of fungi is an order of magnitude larger than bacterial genomes.

Overall Bio-Informatics Analysis:

The Microbiome Analysis Center's Portal was used to organize raw data, track clinical metadata, and track analysis between the groups at baseline and/if they develop infections and are resampled. The portal consists of a Drupal based interface wrapped around a MYSQL database that uses PHP to manage the relational database. The system has built in safeguards to curate the data, keep is secure, and to assure quality control. Raw 16S rRNA and fungal ITS1 gene sequence data were utilized for bioinformatics analysis after chimeric sequences were removed using UChime (Edgar R C, et al. Bioinformatics 2011 27:2194-200). The remaining clean 16S sequences were clustered into operational taxonomic units (OTUs) using the USEARCH algorithm (Edgar R C. Bioinformatics 2010 26:2460-1). A sequence identity of 97% were used to generate OTUs representing bacterial species. The taxonomic identity of reference sequences were determined using the RDP11 Classifier (Wang Q et al. Appl Environ Microbiol 2007 73:5261-7) and QIIME Pipeline. Biostatistical Analysis: Bacterial and fungal community composition were characterized using OTU counts generated as described above. OTU counts were converted to measures of relative abundance to account for variation in sequencing coverage between samples and compared to between groups in the cross-sectional and prospective studies as well as within groups in the prospective study. Statistical analysis was carried out using the statistical software package R (www.r-project.org). Alpha (α) diversity (richness and evenness of taxa within a population) were reported using the Shannon Index (Shannon C E. Bell System Technical Journal 1948 27:379-423). Changes in abundance of individual bacterial and fungal taxa were also analyzed using traditional univariate statistical methods. LEfSe was used to determine the features most likely to explain differences between the subject groups (Segata N, et al. Genome Biol 2011 12:R60).

Results

Cross-Sectional Study 143 patients with cirrhosis (77 outpatients, 66 inpatients) and 26 controls were recruited (Table 1). There were 47 infected patients, 22 culture-negative and 25 with culture-positive infections (Table 4). Culture-positive infections were urinary tract infections (n=8, *Escherichia coli* 3, *Enterococcus* 2, *Candida* 3), *Clostridium difficile* (n=6), spontaneous bacterial peritonitis (SBP, n=6, *Klebsiella* 2, *E. coli* 2, *Candida* 2), SB empyema (n=1, *Staphylococcus*), bacteraemia (n=3, *Staphylococcus aureus* n=1, *Candida* n=2) and one joint infection with *S. aureus*. Of the 22 culture-negative infections, most (n=17) had SBP, three had pneumonia and two had cellulitis. Uninfected Patients were hospitalized for ascites (n=13) and liver transplant evaluation (n=6). Second-generation cephalosporins were used in 21 patients and fluoroquinolones in the rest of the infected patients for median one dose prior. The patients who had *Candida* infections were sampled before antifungal therapies were initiated.

TABLE 1

Demographics and cirrhosis characteristics of subjects in the cross-sectional study

| | Controls (n = 26) | Outpatients (n = 77) | Inpatients (n = 66) |
|---|---|---|---|
| Age (years) | 52.8 ± 8.4 | 55.9 ± 5.6 | 55.3 ± 10.2 |
| Gender (men/women) | 17/9 | 58/19 | 46/20 |
| Aetiology (HCV, alcohol, HCV + alcohol, NAFLD, others) | — | 33/9/8/18/9 | 16/17/15/11/7 |
| MELD score | — | 13.3 ± 6.6 | 19.8 ± 6.4* |
| Prior hepatic encephalopathy | — | 22 (28%) | 40 (61%)* |
| Lactulose alone/any rifaximin | — | 8/14 | 16/24* |
| SBP prophylaxis | — | 12 (15%) | 4 (6%)* |
| Proton pump inhibitors | 0 (0%) | 30 (39%) | 38 (58%) |
| Non-selective beta-blockers | 0 (0%) | 27 | 16 (57%) |
| Diabetes | 0 (0%) | 33 | 18 |
| Infection (none/culture positive/culture negative) | — | 0 (0%) | 19/22/25 |
| Endotoxin levels (EU/mL) | 0.01 ± 0.03 | 0.08 ± 0.03 | 0.19 ± 0.10* |

*$p < 0.05$ on analysis of variance or Kruskal-Wallis depending on data type.
MELD, model for end-stage liver disease;
NALFD; non alcoholic fatty liver disease;
SBP, spontaneous bacterial peritonitis.

TABLE 4

Comparison between the three inpatient groups

| | No infection (n = 19) | Culture negative infection (n = 22) | Culture positive infection (n = 25) |
|---|---|---|---|
| Age (years) | 54.9 ± 9.6 | 55.3 ± 8.9 | 56.4 ± 8.9 |
| Gender (men/women) | 11/8 | 14/8 | 20/5 |
| Etiology (HCV, alcohol, HCV + alcohol, NAFLD, others) | 3/4/2/6/4 | 6/5/7/2/0 | 7/7/5/3/2/1 |
| MELD score | 20.5 ± 6.6 | 17.8 ± 5.9 | 20.8 ± 6.4 |
| Prior Hepatic encephalopathy | 9 | 13 | 18* |
| Lactulose only/Any Rifaximin | 5/4 | 5/8 | 6/12 |
| SBP prophylaxis | 1 | 0 | 3 |
| Proton Pump Inhibitors | 8 | 15 | 15 |
| Non-selective beta-blockers | 4 | 6 | 6 |
| Diabetes | 6 | 6 | 6 |

Bacterial Profiles in Those with Higher Fungal Diversity

Low fungal diversity was defined as a Shannon index of <1, 38% of subjects had low fungi compared with others. These patients had a lower relative abundance of Streptococcaceae, Clostridiales Cluster XIV and Bacillaceae with higher Enterococcaceae and Clostridiaceae.

Fungal and Bacterial Diversity Changes with Setting

Figure 1B:
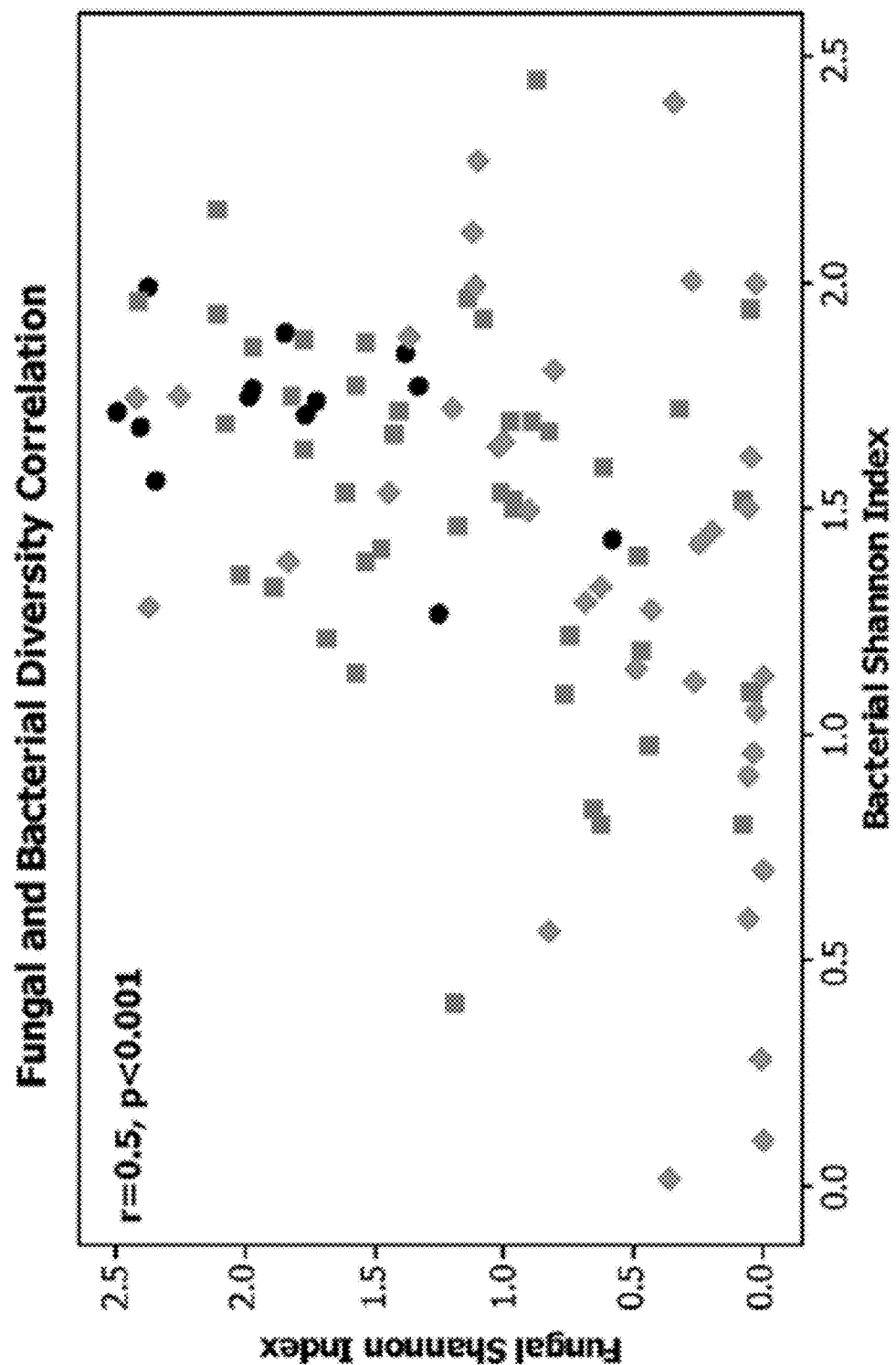

Controls had the highest fungal and bacterial diversity and inpatients the lowest indices (FIG. 1A). There was a negative correlation between MELD score and fungal (r=−0.4, p=0.002) and bacterial (r=−0.43, p<0.001) Shannon diversity indices. There was also a significant correlation between fungal and bacterial diversity (FIG. 1B). Since patients on rifaximin and SBP prophylaxis had a higher model for end-stage liver disease (MELD) score than the rest (Tables 5 and 6), therefore to define the role of absorbable and non-absorbable antibiotics, SBP prophylaxis was compared with rifaximin without prophylaxis. These groups had a similar median MELD score (rifaximin 20 vs SBPP 19) without any change in fungal (rifaximin 0.77±0.77 vs SBPP 0.83±0.60) or bacterial (rifaximin 1.32±0.51 vs SBPP 1.3±0.5) diversity. Therefore, the SBP prophylaxis and rifaximin groups were combined as 'outpatient antibiotics'.

TABLE 5

Comparison between outpatients on and not on SBP prophylaxis

| Outpatients | Not on SBP prophylaxis (n = 65) | On SBP Prophylaxis (n = 12) |
|---|---|---|
| Age (years) | 58.3 ± 5.3 | 55.7 ± 7.7 |
| Gender (men/women) | 48/17 | 10/2 |
| Etiology (HCV, alcohol, HCV + alcohol, NAFLD, others) | 30/8/10/14/8 | 3/3/1/4/1 |
| MELD score | 12.4 ± 6.4 | 17.6 ± 6.6* |
| Prior Hepatic encephalopathy | 14 | 7* |
| Lactulose/Lactulose + Rifaximin | 1/13 | 1/6* |
| Proton Pump Inhibitors | 33 | 5 |
| Non-selective beta-blockers | 23 | 4 |
| Diabetes | 29 | 4 |

TABLE 6

Comparison between outpatients on and not on rifaximin

| Outpatients | Not on rifaximin (n = 63) | Rifaximine use (n = 14) |
|---|---|---|
| Age (years) | 58.6 ± 4.3 | 55.1 ± 9.2 |
| Gender (men/women) | 45/17 | 12/2 |
| Etiology (HCV, alcohol, HCV + alcohol, NAFLD, others) | 27/10/11/16/13 | 6/2/1/2/3 |
| MELD score | 11.9 ± 6.3 | 18.8 ± 5.2* |
| Prior Hepatic encephalopathy | 8 | 14 |
| Lactulose use | 8 | 8 |
| SBP prophylaxis | 6 | 6* |
| Proton Pump Inhibitors | 24 | 6 |
| Non-selective beta-blockers | 21 | 6 |
| Diabetes | 29 | 4 |

Figure 1C:
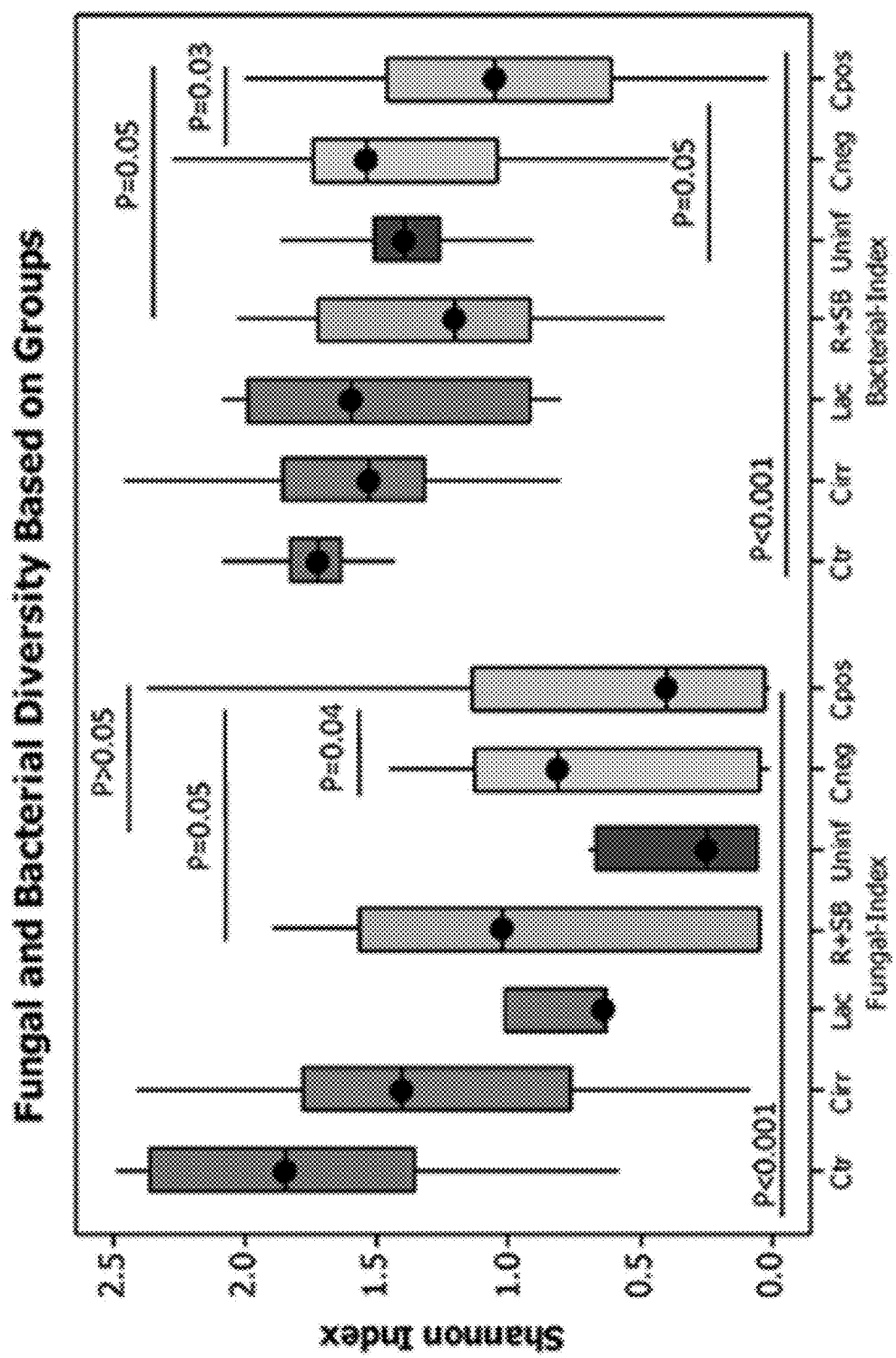

Bacterial diversity in outpatient cirrhotics was lowest in those on antibiotics and within inpatients in patients with culture-positive infections (FIG. 1C). When outpatients on antibiotics were compared with patients with culture-positive infections, there was lower fungal and bacterial diversity in the patients with culture-positive infections (FIG. 1C). Endotoxin was correlated with MELD score (r=0.5, p=0.03) but even though inpatients had a higher endotoxin (Table 1), there was no significant correlation with fungal diversity (r=0.1, p=0.73), while the bacterial diversity was marginally related (r=−0.4, p=0.05). There was no impact of diabetes on bacterial (yes 1.51±0.41 vs no 1.44±0.48, p=0.45) or fungal (yes 1.18±0.75 vs no 1.02±0.78, p=0.47) diversity indices.

Individual Bacterial and Fungal Phyla are Linked

The major fungal phyla, Ascomycota and Basidiomycota, were studied in relation to Bacteroidetes, Firmicutes and Proteobacteria in the entire cohort. As expected, there was a significant linkage between MELD score and Proteobacteria (r=0.4, p<0.0001) and Bacteroidetes (r=−0.4, p=0.014) but neither of the major fungal phyla nor Firmicutes were significantly linked to the MELD score. Ascomycota were negatively correlated with Bacteroidetes (r=−0.2, p=0.03). However, the Basidiomycota/Ascomycota ratio was positively correlated with MELD (r=0.3, p=0.05). Proteobacteria were negatively correlated (r=−0.3, p<0.001) with Firmicutes and to Bacteroidetes (p=−0.5, p<0.001). Bacteroidetes were also negatively linked with Firmicutes (r=−0.7, p<0.001).

Bacterial and Fungal Profiles were Different Between the Groups on LEFSe

Figure 2A:
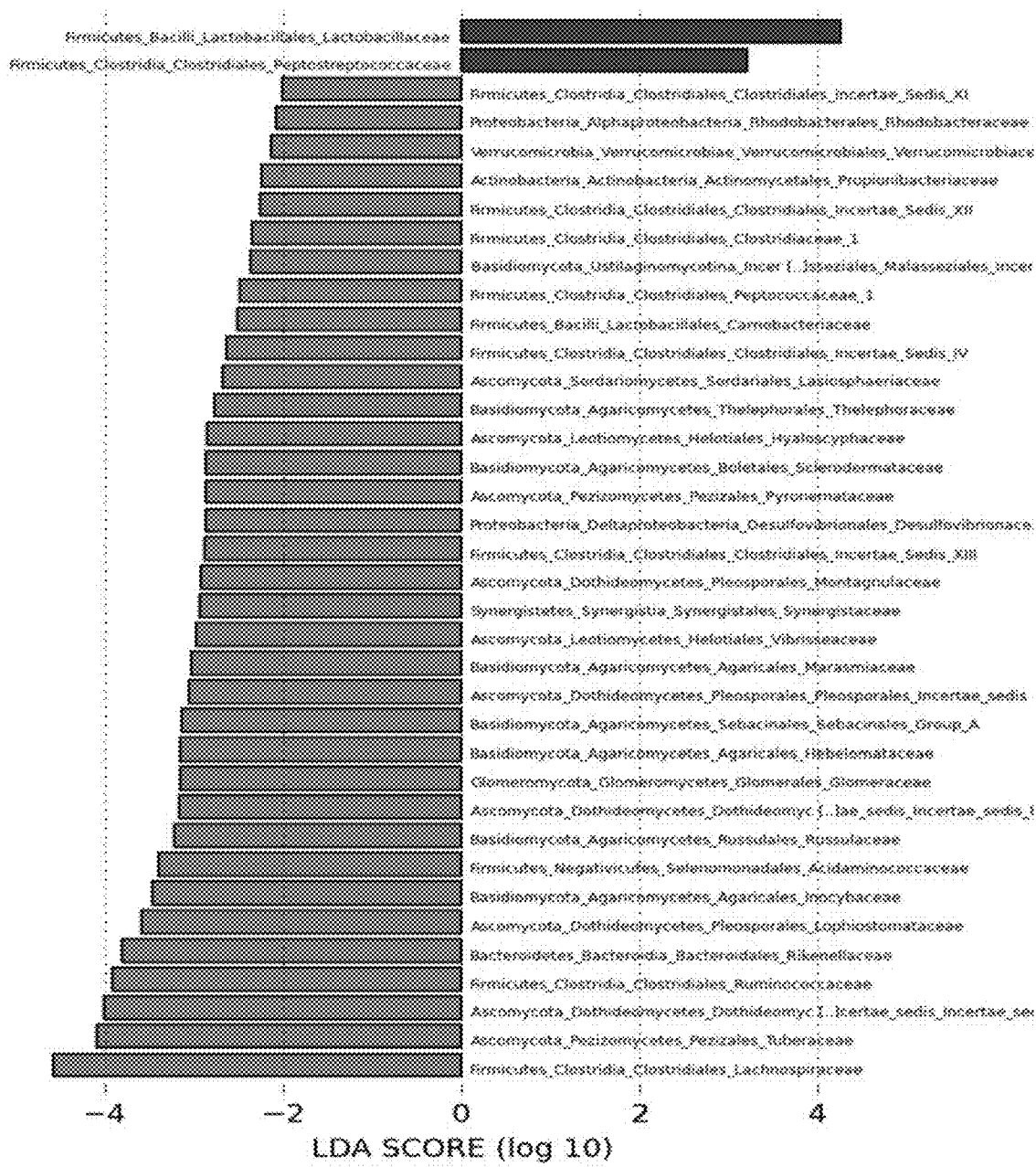
FIG. 2. Cross-sectional study using linear discriminant analysis effect size (LEFSe). Specific changes in bacterial and fungal relative abundance between the three groups using LEFSe, Cirrhosis_No_antibiotics: Uninfected cirrhotics, Cirrhosis_Antibiotics: infected patients with cirrhosis, Controls: healthy controls. (A) Comparison between outpatients with cirrhosis (green) and healthy controls (red), (B) comparison between all inpatients with cirrhosis (green) and healthy controls (red), (C) comparison between outpatients with cirrhosis (green) and inpatients with cirrhosis (red), (D) comparison between outpatients with cirrhosis on antibiotics (rifaximin and spontaneous bacterial peritonitis prophylaxis; red) compared with outpatients with cirrhosis not on these medications (green).
Figure 2B:
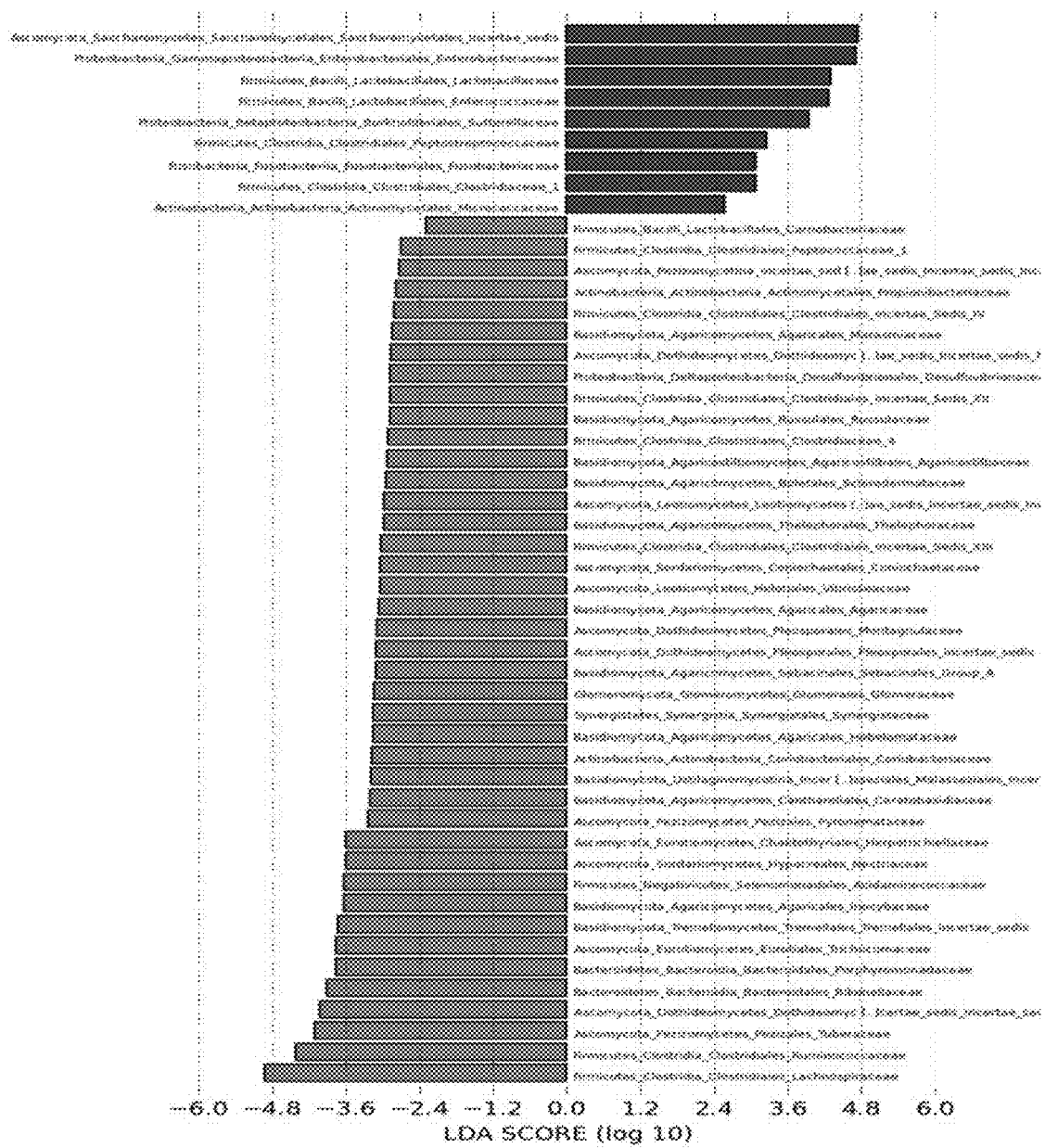
Figure 2C:
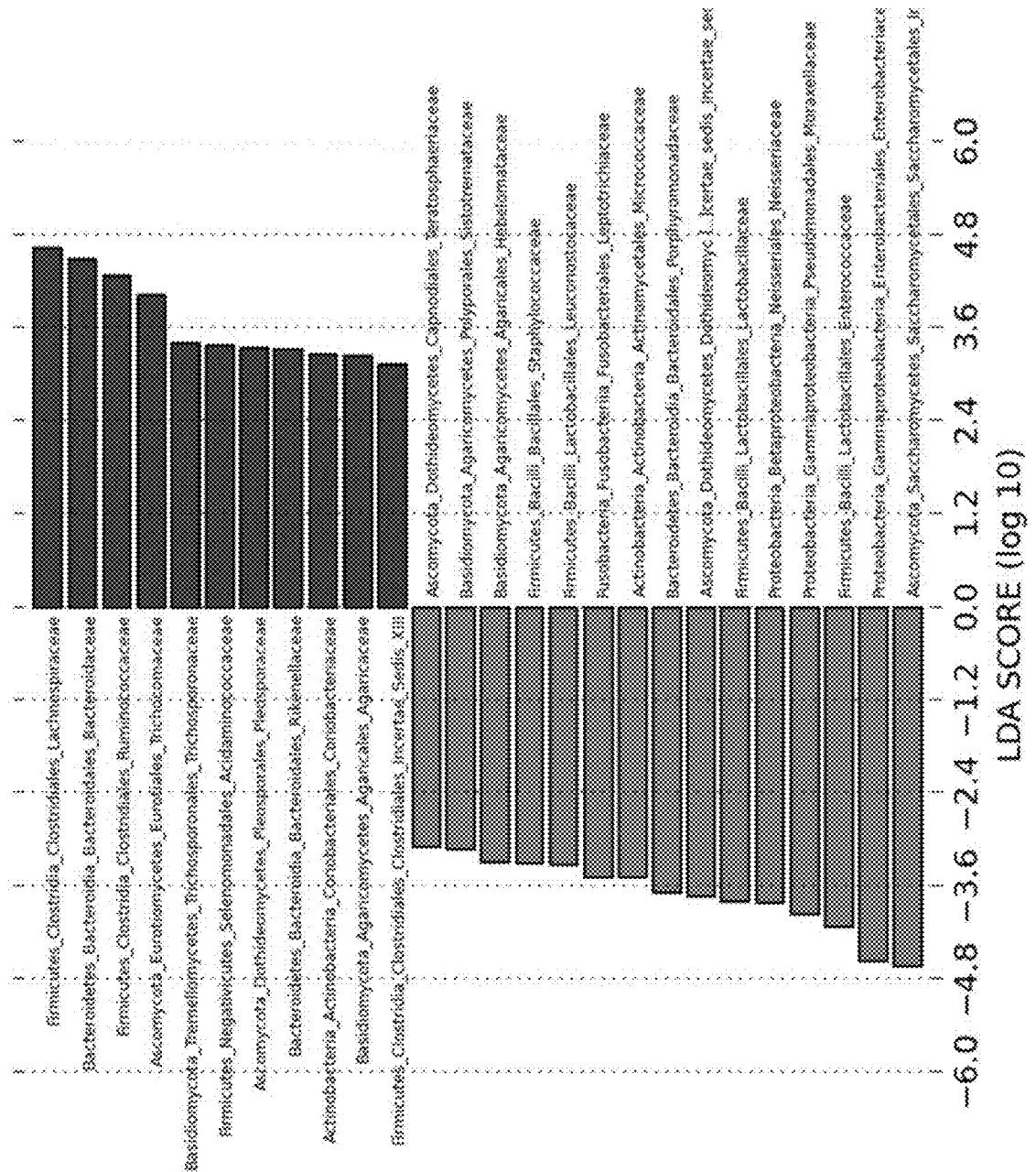

Healthy controls had a significantly higher relative abundance of autochthonous bacterial taxa as well as diverse fungi, including members of Basidiomycota when compared with outpatient cirrhotics (FIG. 2A). Similar findings were seen when healthy controls were compared with inpatients, except with a significantly higher relative abundance of Candida and potentially pathogenic bacterial taxa such as Enterobacteriaceae and Enterococcaceae in inpatients (FIG. 2B). When inpatients were compared with outpatients, a higher relative abundance of Candida, Enterobacteriaceae and Enterococcaceae was found in inpatients with a lower autochthonous bacterial taxa and members of Basidiomycota.

Figure 2D:
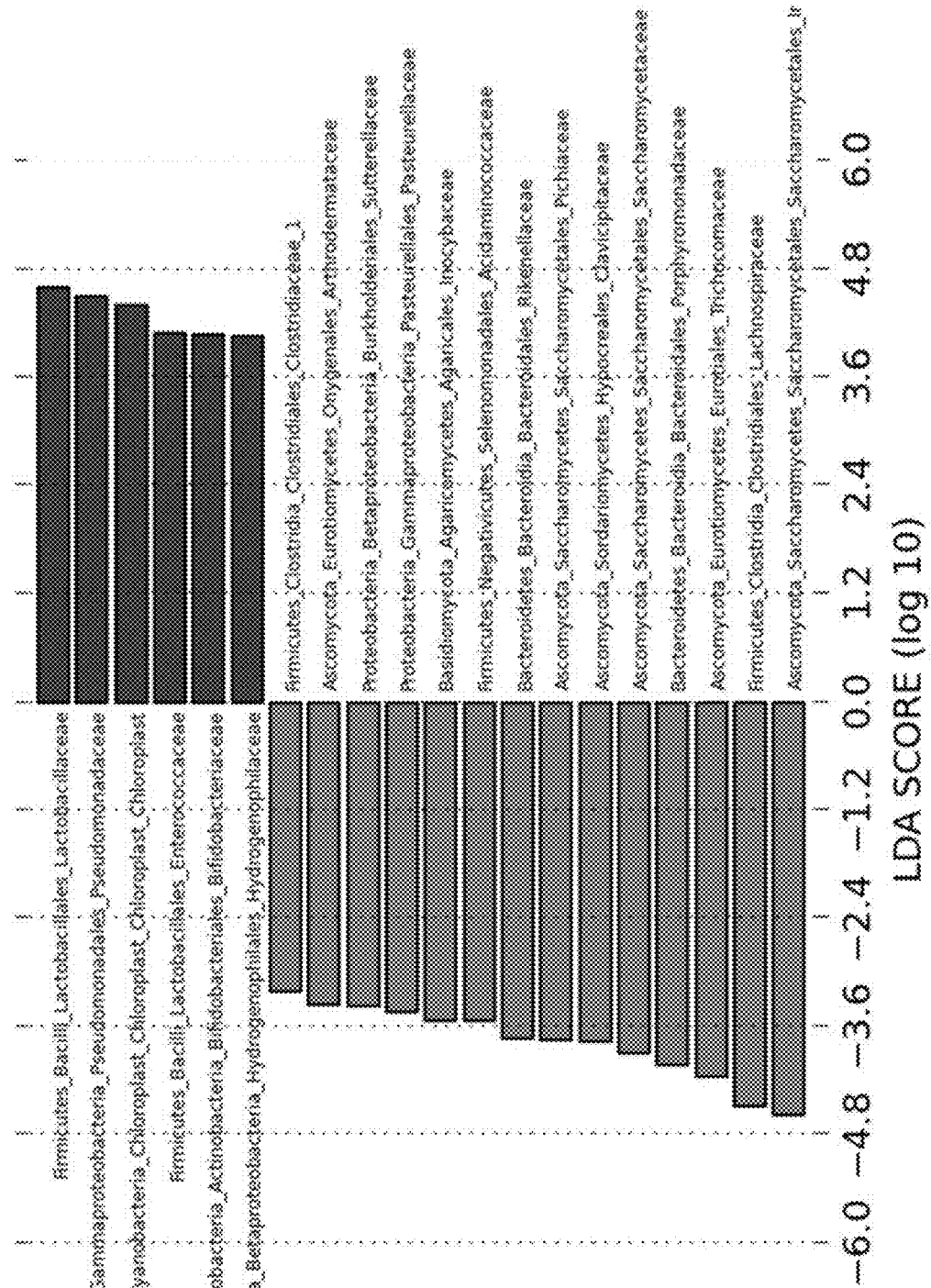

Outpatients on antibiotics were more likely to have higher potentially pathogenic taxa such as Pasteurellaceae, and several members of Ascomycota, including Candida (FIG. 2D). This trend continued broadly with more Candida and fungi in infected patients, especially in culture-negative infections compared with culture-positive infections (Tables 7-10).

TABLE 7

LEFSe Comparison between inpatients

| Phylum_Order_Family_Genus | Group with higher LDA | P value |
|---|---|---|
| Admitted without infection vs. Admitted with Culture negative infection | | |
| Bacteroidetes_Bacteroidia_Bacteroidales_Bacteroidaceae | Uninfected | 0.03 |
| Basidiomycota_Ustilaginomycetes_Ustilaginales_Ustilaginales_Incertaesedis | Uninfected | 0.04 |
| Ascomycota_Eurotiomycetes_Onygenales_Arthrodermataceae | Culture negative | 0.04 |
| Ascomycota_Pezizomycetes_Pezizales_Tuberaceae | Culture negative | 0.012 |
| Ascomycota_Dothideomycetes_Pleosporales_Venturiaceae | Culture negative | 0.04 |
| Ascomycota_Sordariomycetes_Hypocreales_Clavicipitaceae | Culture negative | 0.012 |
| Firmicutes_Bacilli_Lactobacillales_Leuconostocaceae | Culture negative | 0.012 |

TABLE 7-continued

LEFSe Comparison between inpatients

| Phylum_Order_Family_Genus | Group with higher LDA | P value |
|---|---|---|
| Admitted without infection vs. Admitted with Culture positive infection | | |
| Firmicutes_Clostridia_Clostridiales_Clostridiales_IncertaeSedisXI | Uninfected | 0.015 |
| Firmicutes_Clostridia_Clostridiales_Ruminococcaceae | Uninfected | 0.005 |
| Firmicutes_Erysipelotrichia_Erysipelotrichales_Erysipelotrichaceae | Uninfected | 0.04 |
| Firmicutes_Clostridia_Clostridiales_Lachnospiraceae | Uninfected | 0.005 |
| Admitted with culture-negative infection vs. Admitted with Culture positive infection | | |
| Proteobacteria_Deltaproteobacteria_Desulfovibrionales_Desulfovibrionaceae | Culture negative | 0.002 |
| Ascomycota_Sordariomycetes_Hypocreomycetidae_Incertaesedis_Plectosphaerellaceae | Culture negative | 0.02 |
| Ascomycota_Sordariomycetes_Hypocreales_Clavicipitaceae | Culture negative | 0.013 |
| Firmicutes_Clostridia_Clostridiales_Ruminococcaceae | Culture negative | 0.006 |
| Basidiomycota_Agaricomycetes_Polyporales_Sistotremataceae | Culture negative | 0.02 |
| Firmicutes_Clostridia_Clostridiales_Lachnospiraceae | Culture negative | 0.005 |
| Bacteroidetes_Bacteroidia_Bacteroidales_Rikenellaceae | Culture negative | 0.018 |

TABLE 8

LEFSe Comparison between cirrhotic outpatients

| Phylum_Order_Family_Genus | Group with higher LDA | P value |
|---|---|---|
| Outpatient not on anything vs outpatient on lactulose only | | |
| Bacteroidetes_Bacteroidia_Bacteroidales_Porphyromonadaceae | Not on anything | 0.014 |
| Bacteroidetes_Bacteroidia_Bacteroidales_Rikenellaceae | Not on anything | 0.03 |
| Bacteroidetes_Bacteroidia_Bacteroidales_Bacteroidaceae | Not on anything | 0.029 |
| Ascomycota_Eurotiomycetes_Eurotiales_Trichocomaceae | On lactulose | 0.012 |
| Ascomycota_Sordariomycetes_Hypocreales_Hypocreaceae | On lactulose | 0.01 |
| Firmicutes_Bacilli_Bacillales_Bacillales_IncertaeSedisXI | On lactulose | 0.01 |
| Ascomycota_Eurotiomycetes_Pyrenulales_Massariaceae | On lactulose | 0.01 |
| Firmicutes_Bacilli_Lactobacillales_Carnobacteriaceae | On lactulose | 0.032 |
| Proteobacteria_Gammaproteobacteria_Pseudomonadales_Pseudomonadaceae | On lactulose | 0.01 |
| Basidiomycota_Agaricomycetes_Agaricales_Hebelomataceae | On lactulose | 0.014 |
| Ascomycota_Lecanoromycetes_Lecanorales_Parmeliaceae | On lactulose | 0.0002 |
| Basidiomycota_Agaricomycetes_Agaricomycetidae_Incertaesedis_Agaricomycetidae_Incertaesedis_Incertaesedis | On lactulose | 0.0002 |
| Actinobacteria_Actinobacteria_Bifidobacteriales_Bifidobacteriaceae | On lactulose | 0.001 |
| Bacteroidetes_Flavobacteriia_Flavobacteriales_Flavobacteriaceae | On lactulose | 0.0103 |
| Outpatient not on anything vs outpatient on rifaximin (no SBPP) | | |
| Ascomycota_Sordariomycetes_Microascales_Halosphaeriaceae | On rifaximin | 9.01E-05 |
| Basidiomycota_Agaricomycetes_Polyporales_Meruliaceae | On rifaximin | 0.010 |
| Zygomycota_Mucoromycotina_Incertaesedis_Mucorales_Phycomycetaceae | On rifaximin | 9.01E-05 |
| Basidiomycota_Agaricomycetes_Agaricomycetidae_Incertaesedis_Agaricomycetidae_Incertaesedis_Incertaesedis | On rifaximin | 9.01E-05 |
| Chytridiomycota_Chytridiomycetes_Rhizophydiales_Rhizophydiaceae | On rifaximin | 9.01E-05 |
| Outpatient not on anything vs outpatient on SBP prophylaxis | | |
| Basidiomycota_Agaricostilbomycetes_Agaricostilbales_Agaricostilbaceae | On SBPP | 0.03 |
| Proteobacteria_Gammaproteobacteria_Aeromonadales_Succinivibrionaceae | On SBPP | 1.62E-06 |
| Proteobacteria_Epsilonproteobacteria_Campylobacterales_Campylobacteraceae | On SBPP | 0.0008 |
| Bacteroidetes_Bacteroidia_Bacteroidales_Marinilabiliaceae | On SBPP | 0.001 |
| Basidiomycota_Agaricomycetes_Sebacinales_SebacinalesGroupA | On SBPP | 1.62E-06 |
| Outpatient not on anything vs outpatient on lactulose, rifaximin and SBP prophylaxis | | |
| Bacteroidetes_Bacteroidia_Bacteroidales_Porphyromonadaceae | Not on anything | 0.049 |
| Bacteroidetes_Bacteroidia_Bacteroidales_Rikenellaceae | Not on anything | 0.027 |
| Proteobacteria_Betaproteobacteria_Burkholderiales_Sutterellaceae | Not on anything | 0.02 |
| Ascomycota_Eurotiomycetes_Onygenales_Arthrodermataceae | On L, R, SBPP | 0.099 |
| Ascomycota_Eurotiomycetes_Eurotiales_Trichocomaceae | On L, R, SBPP | 0.03 |
| Ascomycota_Saccharomycetes_Saccharomycetales_Saccharomycetaceae | On L, R, SBPP | 0.02 |
| Proteobacteria_Epsilonproteobacteria_Campylobacterales_Campylobacteraceae | On L, R, SBPP | 0.04 |
| Firmicutes_Bacilli_Lactobacillales_Enterococcaceae | On L, R, SBPP | 4.59E-05 |
| Proteobacteria_Betaproteobacteria_Burkholderiales_Burkholderiales_Incertae_sedis | On L, R, SBPP | 0.046 |
| Proteobacteria_Gammaproteobacteria_Xanthomonadales_Xanthomonadaceae | On L, R, SBPP | 0.002 |
| Firmicutes_Bacilli_Lactobacillales_Lactobacillaceae | On L, R, SBPP | 0.04 |
| Actinobacteria_Actinobacteria_Actinomycetales_Promicromonosporaceae | On L, R, SBPP | 0.002 |
| Proteobacteria_Betaproteobacteria_Burkholderiales_Comamonadaceae | On L, R, SBPP | 0.001 |
| Actinobacteria_Actinobacteria_Actinomycetales_Corynebacteriaceae | On L, R, SBPP | 0.002 |

TABLE 8-continued

LEFSe Comparison between cirrhotic outpatients

| Phylum_Order_Family_Genus | Group with higher LDA | P value |
|---|---|---|
| Actinobacteria_Actinobacteria_Actinomycetales_Propionibacteriaceae | On L, R, SBPP | 0.002 |
| Proteobacteria_Betaproteobacteria_Hydrogenophilales_Hydrogenophilaceae | On L, R, SBPP | 0.002 |
| Firmicutes_Erysipelotrichia_Erysipelotrichales_Erysipelotrichaceae | On L, R, SBPP | 0.03 |

TABLE 9

LEFSe Comparison_Between healthy controls and outpatient cirrhosis

| Phylum_Order_Family_Genus | Group with higher LDA | P value |
|---|---|---|
| *Healthy controls vs. outpatients not on anything* | | |
| Basidiomycota_Agaricomycetes_Agaricales_Marasmiaceae | Controls | 0.03 |
| Basidiomycota_Agaricomycetes_Thelephorales_Thelephoraceae | Controls | 0.009 |
| Proteobacteria_Deltaproteobacteria_Desulfovibrionales_Desulfovibrionaceae | Controls | 0.04 |
| Ascomycota_Pezizomycetes_Pezizales_Tuberaceae | Controls | 0.02 |
| Ascomycota_Dothideomycetes_Pleosporales_Lophiostomataceae | Controls | 0.007 |
| Ascomycota_Dothideomycetes_Dothideomycetes_Incertaesedis_Incertaesedis_Gloniaceae | Controls | 1.29E−06 |
| Firmicutes_Clostridia_Clostridiales_Peptostreptococcaceae | Controls | 0.04 |
| Ascomycota_Dothideomycetes_Pleosporales_Montagnulaceae | Controls | 0.03 |
| Synergistetes_Synergistia_Synergistales_Synergistaceae | Controls | 0.002 |
| Basidiomycota_Agaricomycetes_Russulales_Russulaceae | Controls | 0.03 |
| Bacteroidetes_Bacteroidia_Bacteroidales_Rikenellaceae | Controls | 0.009 |
| Firmicutes_Clostridia_Clostridiales_Clostridiales_IncertaeSedisXII | Controls | 0.002 |
| Firmicutes_Bacilli_Lactobacillales_Carnobacteriaceae | Controls | 0.002 |
| Basidiomycota_Agaricomycetes_Boletales_Sclerodermataceae | Controls | 1.23E−05 |
| Firmicutes_Clostridia_Clostridiales_Peptococcaceaeel | Controls | 0.01 |
| Firmicutes_Clostridia_Clostridiales_Clostridiales_IncertaeSedisIV | Controls | 0.0002 |
| Firmicutes_Clostridia_Clostridiales_Clostridiales_IncertaeSedisXI | Controls | 0.01 |
| Basidiomycota_Agaricomycetes_Sebacinales_SebacinalesGroupA | Controls | 0.001 |
| Basidiomycota_Agaricomycetes_Agaricales_Hebelomataceae | Controls | 2.63E−05 |
| Firmicutes_Clostridia_Clostridiales_Clostridiales_IncertaeSedisXIII | Controls | 0.006 |
| Ascomycota_Pezizomycetes_Pezizales_Pyronemataceae | Controls | 0.01 |
| Actinobacteria_Actinobacteria_Actinomycetales_Propionibacteriaceae | Controls | 0.0004 |
| Ascomycota_Dothideomycetes_Dothideomycetes_Incertaesedis_Incertaesedis_Myxotrichaceae | Controls | 0.03 |
| Glomeromycota_Glomeromycetes_Glomerales_Glomeraceae | Controls | 0.03 |
| Firmicutes_Clostridia_Clostridiales_Lachnospiraceae | Controls | 0.006 |
| Firmicutes_Bacilli_Lactobacillales_Enterococcaceae | Not on anything | 0.04 |
| Proteobacteria_Gammaproteobacteria_Enterobacteriales_Enterobacteriaceae | Not on anything | 0.01 |
| Ascomycota_Sordariomycetes_Hypocreales_Clavicipitaceae | Not on anything | 0.02 |
| *Healthy controls vs. outpatients on lactulose only* | | |
| Proteobacteria_Deltaproteobacteria_Desulfovibrionales_Desulfovibrionaceae | Controls | 0.04 |
| Ascomycota_Sordariomycetes_Hypocreales_Nectriaceae | Controls | 0.04 |
| Ascomycota_Dothideomycetes_Dothideomycetes_Incertaesedis_Incertaesedis_Gloniaceae | Controls | 0.04 |
| Bacteroidetes_Bacteroidia_Bacteroidales_Porphyromonadaceae | Controls | 0.01 |
| Firmicutes_Clostridia_Clostridiales_Peptostreptococcaceae | Controls | 0.009 |
| Bacteroidetes_Bacteroidia_Bacteroidales_Rikenellaceae | Controls | 0.004 |
| Firmicutes_Clostridia_Clostridiales_Clostridiales_IncertaeSedisXIII | Controls | 0.02 |
| Ascomycota_Eurotiomycetes_Eurotiales_Trichocomaceae | Controls | 0.02 |
| Fusobacteria_Fusobacterfia_Fusobacteriales_Fusobacteriaceae | On Lactulose | 0.002 |
| Basidiomycota_Agaricomycetes_Agaricomycetidae_Incertaesedis_Agaricomycetidae_Incertaesedis_Incertaesedis | On Lactulose | |
| Actinobacteria_Actinobacteria_Bifidobacteriales_Bifidobacteriaceae | On Lactulose | 0.01 |
| *Healthy controls vs. outpatients on rifaximin (no SBPP)* | | |
| Proteobacteria_Deltaproteobacteria_Desulfovibrionaceae_Desulfovibrionales | Controls | 0.03 |
| Ascomycota_Pezizomycetes_Pezizales_Tuberaceae | Controls | 0.04 |
| Ascomycota_Dothideomycetes_Dothideomycetes_Incertaesedis_Incertaesedis_Gloniaceae | Controls | 0.01 |
| Bacteroidetes_Bacteroidia_Bacteroidales_Porphyromonadaceae | Controls | 0.0003 |
| Basidiomycota_Agaricomycetes_Agaricales_Inocybaceae | Controls | 0.01 |
| Firmicutes_Clostridia_Clostridiales_Peptostreptococcaceae | Controls | 0.01 |
| Bacteroidetes_Bacteroidia_Bacteroidales_Rikenellaceae | Controls | 0.0007 |
| Firmicutes_Bacilli_Lactobacillales_Carnobacteriaceae | Controls | 0.03 |
| Basidiomycota_Agaricomycetes_Boletales_Sclerodermataceae | Controls | 0.01 |
| Firmicutes_Clostridia_Clostridiales_Clostridiaceael | Controls | 0.009 |

TABLE 9-continued

LEFSe Comparison Between healthy controls and outpatient cirrhosis

| Phylum_Order_Family_Genus | Group with higher LDA | P value |
|---|---|---|
| Firmicutes_Clostridia_Clostridiales_Clostridiales_IncertaeSedisIV | Controls | 0.04 |
| Basidiomycota_Agaricomycetes_Agaricales_Hebelomataceae | Controls | 0.04 |
| Firmicutes_Clostridia_Clostridiales_Ruminococcaceae | Controls | 0.009 |
| Firmicutes_Negativicutes_Selenomonadales_Acidaminococcaceae | Controls | 0.007 |
| Firmicutes_Clostridia_Clostridiales_Clostridiales_IncertaeSedisXIII | Controls | 0.008 |
| Proteobacteria_Betaproteobacteria_Burkholderiales_Sutterellaceae | Controls | 0.02 |
| Firmicutes_Clostridia_Clostridiales_Lachnospiraceae | Controls | 0.0001 |
| Actinobacteria_Actinobacteria_Actinomycetales_Micrococcaceae | On Rifaximin | 0.04 |
| Firmicutes_Bacilli_Lactobacillales_Lactobacillaceae | On Rifaximin | 0.002 |
| Proteobacteria_Gammaproteobacteria_Pseudomonadales_Pseudomonadaceae | On Rifaximin | 0.04 |
| Healthy controls vs. outpatient on lactulose, rifaximin and SBP prophylaxis | | |
| Proteobacteria_Deltaproteobacteria_Desulfovibrionales_Desulfovibrionaceae | Controls | 0.02 |
| Bacteroidetes_Bacteroidia_Bacteroidales_Porphyromonadaceae | Controls | 0.02 |
| Basidiomycota_Agaricomycetes_Agaricales_Inocybaceae | Controls | 0.04 |
| Bacteroidetes_Bacteroidia_Bacteroidales_Rikenellaceae | Controls | 0.002 |
| Ascomycota_Eurotiomycetes_Onygenales_Arthrodermataceae | Controls | 0.02 |
| Ascomycota_Saccharomycetes_Saccharomycetales_Saccharomycetaceae | Controls | 0.04 |
| Actinobacteria_Actinobacteria_Coriobacteriales_Coriobacteriaceae | Controls | 0.04 |
| Firmicutes_Negativicutes_Selenomonadales_Acidaminococcaceae | Controls | 0.02 |
| Firmicutes_Clostridia_Clostridiales_Clostridiales_IncertaeSedisXIII | Controls | 0.01 |
| Proteobacteria_Betaproteobacteria_Burkholderiales_Sutterellaceae | Controls | 0.01 |
| Firmicutes_Clostridia_Clostridiales_Lachnospiraceae | Controls | 0.03 |
| Proteobacteria_Epsilonproteobacteria_Campylobacterales_Campylobacteraceae | On L, R, SBPP | 0.04 |
| Firmicutes_Bacilli_Lactobacillales_Enterococcaceae | On L, R, SBPP | 0.021397569 |
| Proteobacteria_Gammaproteobacteria_Xanthomonadales_Xanthomonadaceae | On L, R, SBPP | 0.04 |
| Firmicutes_Bacilli_Lactobacillales_Lactobacillaceae | On L, R, SBPP | 0.01 |
| Actinobacteria_Actinobacteria_Actinomycetales_Promicromonosporaceae | On L, R, SBPP | 0.04 |
| Proteobacteria_Betaproteobacteria_Burkholderiales_Comamonadaceae | On L, R, SBPP | 0.04 |
| Actinobacteria_Actinobacteria_Actinomycetales_Actinomycetaceae | On L, R, SBPP | 0.04 |
| Actinobacteria_Actinobacteria_Actinomycetales_Corynebacteriaceae | On L, R, SBPP | 0.04 |
| Proteobacteria_Betaproteobacteria_Hydrogenophilales_Hydrogenophilaceae | On L, R, SBPP | 0.04 |

TABLE 10

LEFSe Comparison between healthy controls and inpatient cirrhosis

| Phylum_Order_Family_Genus | Group with higher LDA | P value |
|---|---|---|
| Healthy controls vs. admitted with no infection | | |
| Actinobacteria_Actinobacteria_Actinomycetales_Micrococcaceae | Uninfected | 0.03 |
| Firmicutes_Bacilli_Lactobacillales_Lactobacillaceae | Uninfected | 0.01 |
| Fusobacteria_Fusobacteriia_Fusobacteriales_Fusobacteriaceae | Uninfected | 0.01 |
| Proteobacteria_Gammaproteobacteria_Enterobacteriales_Enterobacteriaceae | Uninfected | 0.001 |
| Actinobacteria_Actinobacteria_Actinomycetales_Actinomycetaceae | Uninfected | 0.012 |
| Basidiomycota_Agaricomycetes_Thelephorales_Thelephoraceae | Controls | 0.04 |
| Proteobacteria_Deltaproteobacteria_Desulfovibrionales_Desulfovibrionaceae | Controls | 0.02 |
| Ascomycota_Pezizomycetes_Pezizales_Tuberaceae | Controls | 0.004 |
| Ascomycota_Sordariomycetes_Hypocreales_Nectriaceae | Controls | 0.01 |
| Ascomycota_Dothideomycetes_Dothideomycetes_Incertaesedis_Incertaesedis_Gloniaceae | Controls | 0.004 |
| Bacteroidetes_Bacteroidia_Bacteroidales_Porphyromonadaceae | Controls | 0.002 |
| Basidiomycota_Agaricomycetes_Agaricales_Inocybaceae | Controls | 0.02 |
| Firmicutes_Clostridia_Clostridiales_Peptostreptococcaceae | Controls | 0.001 |
| Synergistetes_Synergistia_Synergistales_Synergistaceae | Controls | 0.008 |
| Basidiomycota_Tremellomycetes_Tremellales_Tremellales_Incertaesedis | Controls | 0.04 |
| Bacteroidetes_Bacteroidia_Bacteroidales_Rikenellaceae | Controls | 0.0006 |
| Firmicutes_Clostridia_Clostridiales_Clostridiales_IncertaeSedisXII | Controls | 0.04 |

TABLE 10-continued

LEFSe Comparison between healthy controls and inpatient cirrhosis

| Phylum_Order_Family_Genus | Group with higher LDA | P value |
|---|---|---|
| Basidiomycota_Agaricomycetes_Boletales_Sclerodermataceae | Controls | 0.004 |
| Ascomycota_Eurotiomycetes_Onygenales_Arthrodermataceae | Controls | 0.02 |
| Firmicutes_Clostridia_Clostridiales_Clostridiaceae1 | Controls | 0.007 |
| Firmicutes_Clostridia_Clostridiales_Clostridiales_IncertaeSedisIV | Controls | 0.01 |
| Basidiomycota_Agaricomycetes_Agaricales_Hebelomataceae | Controls | 0.01 |
| Firmicutes_Clostridia_Clostridiales_Ruminococcaceae | Controls | 0.0001 |
| Firmicutes_Negativicutes_Selenomonadales_Acidaminococcaceae | Controls | 0.0008 |
| Firmicutes_Clostridia_Clostridiales_Clostridiales_IncertaeSedisXIII | Controls | 0.0001 |
| Ascomycota_Eurotiomycetes_Eurotiales_Trichocomaceae | Controls | 0.002 |
| Actinobacteria_Actinobacteria_Actinomycetales_Propionibacteriaceae | Controls | 0.04 |
| Firmicutes_Clostridia_Clostridiales_Lachnospiraceae | Controls | 7.67E-05 |
| Healthy Controls vs._Admitted with culture-negative infection | | |
| Firmicutes_Clostridia_Clostridiales_Peptostreptococcaceae | Culture negative | 0.03 |
| Proteobacteria_Gammaproteobacteria_Pseudomonadales_Moraxellaceae | Culture negative | 0.03 |
| Actinobacteria_Actinobacteria_Actinomycetales_Micrococcaceae | Culture negative | 0.03 |
| Firmicutes_Bacilli_Lactobacillales_Lactobacillaceae | Culture negative | 0.0003 |
| Firmicutes_Bacilli_Bacillales_Staphylococcaceae | Culture negative | 0.03 |
| Fusobacteria_Fusobacteriia_Fusobacteriales_Fusobacteriaceae | Culture negative | 0.007 |
| Proteobacteria_Gammaproteobacteria_Enterobacteriales_Enterobacteriaceae | Culture negative | 0.0002 |
| Ascomycota_Sordariomycetes_Hypocreales_Clavicipitaceae | Culture negative | 0.003 |
| Firmicutes_Bacilli_Lactobacillales_Leuconostocaceae | Culture negative | 0.01 |
| Basidiomycota_Agaricomycetes_Thelephorales_Thelephoraceae | Controls | 0.027 |
| Ascomycota_Dothideomycetes_Dothideomycetes_Incertaesedis_Incertaesedis_Gloniaceae | Controls | 0.0031 |
| Basidiomycota_Agaricomycetes_Agaricales_Agaricaceae | Controls | 0.04 |
| Bacteroidetes_Bacteroidia_Bacteroidales_Porphyromonadaceae | Controls | 0.03 |
| Synergistetes_Synergistia_Synergistales_Synergistaceae | Controls | 0.009 |
| Bacteroidetes_Bacteroidia_Bacteroidales_Rikenellaceae | Controls | 0.002 |
| Firmicutes_Clostridia_Clostridiales_Clostridiales_IncertaeSedisXII | Controls | 0.02 |
| Firmicutes_Bacilli_Lactobacillales_Carnobacteriaceae | Controls | 0.02 |
| Bacteroidetes_Bacteroidia_Bacteroidales_Bacteroidaceae | Controls | 0.02 |
| Basidiomycota_Ustilaginomycotina_Incertaesedis_Malasseziales_Malasseziales_Incertaesedis | Controls | 0.04 |
| Actinobacteria_Actinobacteria_Coriobacteriales_Coriobacteriaceae | Controls | 0.01 |
| Firmicutes_Clostridia_Clostridiales_Ruminococcaceae | Controls | 8.30E-05 |
| Firmicutes_Negativicutes_Selenomonadales_Acidaminoccceaea | Controls | 0.008 |
| Firmicutes_Clostridia_Clostridiales_Clostridiales_IncertaeSedisXIII | Controls | 0.003 |
| Ascomycota_Eurotiomycetes_Eurotiales_Trichocomaceae | Controls | 0.012 |
| Ascomycota_Pezizomycetes_Pezizales_Pyronemataceae | Controls | 0.04 |
| Healthy controls vs. Admitted with culture-positive infection | | |
| Proteobacteria_Gammaproteobacteria_Aeromonadales_Succinivibrionaceae | Culture positive | 0.002 |
| Basidiomycota_Agaricomycetes_Sebacinales_SebacinalesGroupA | Culture positive | 0.03 |
| Bacteroidetes_Bacteroidia_Bacteroidales_Porphyromonadaceae | Culture positive | 0.0001 |
| Firmicutes_Bacilli_Lactobacillales_Enterococcaceae | Culture positive | 0.005 |
| Actinobacteria_Actinobacteria_Actinomycetales_Micrococcaceae | Culture positive | 0.02 |
| Firmicutes_Bacilli_Lactobacillales_Lactobacillaceae | Culture positive | 0.0005 |
| Firmicutes_Clostridia_Clostridiales_Clostridiaceae1 | Culture positive | 0.02 |
| Fusobacteria_Fusobacteriia_Fusobacteriales_Fusobacteriaceae | Culture positive | 0.02 |
| Proteobacteria_Gammaproteobacteria_Enterobacteriales_Enterobacteriaceae | Culture positive | 0.01 |
| Basidiomycota_Agaricomycetes_Thelephorales_Thelephoraceae | Controls | 0.01 |
| Proteobacteria_Deltaproteobacteria_Desulfovibrionales_Desulfovibrionaceae | Controls | 0.0001 |
| Ascomycota_Dothideomycetes_Dothideomycetes_Incertaesedis_Incertaesedis_Gloniaceae | Controls | 0.02 |
| Basidiomycota_Agaricomycetes_Agaricales_Agaricaceae | Controls | 0.03 |
| Basidiomycota_Agaricomycetes_Agaricales_Inocybaceae | Controls | 0.007 |
| Firmicutes_Clostridia_Clostridiales_Peptostreptococcaceae | Controls | 0.0004 |
| Synergistetes_Synergistia_Synergistales_Synergistaceae | Controls | 0.01 |
| Bacteroidetes_Bacteroidia_Bacteroidales_Rikenellaceae | Controls | 2.76E-07 |

TABLE 10-continued

LEFSe Comparison between healthy controls and inpatient cirrhosis

| Phylum_Order_Family_Genus | Group with higher LDA | P value |
|---|---|---|
| Basidiomycota_Agaricomycetes_Boletales_Sclerodermataceae | Controls | 0.004 |
| Firmicutes_Clostridia_Clostridiales_Peptococcaceae1 | Controls | 0.03 |
| Firmicutes_Clostridia_Clostridiales_Clostridiales_IncertaeSedisIV | Controls | 0.01 |
| Firmicutes_Clostridia_Clostridiales_Clostridiales_IncertaeSedisXI | Controls | 0.03 |
| Ascomycota_Saccharomycetes_Saccharomycetales_Dipodascaceae | Controls | 0.03 |
| Actinobacteria_Actinobacteria_Coriobacteriales_Coriobacteriaceae | Controls | 0.0007 |
| Firmicutes_Clostridia_Clostridiales_Ruminococcaceae | Controls | 1.11E−06 |
| Firmicutes_Negativicutes_Selenomonadales_Acidaminococcaceae | Controls | 8.25E−05 |
| Firmicutes_Clostridia_Clostridiales_Clostridiales_IncertaeSedisXIII | Controls | 7.56E−05 |
| Ascomycota_Eurotiomycetes_Eurotiales_Trichocomaceae | Controls | 0.02 |
| Ascomycota_Pezizomycetes_Pezizales_Pyronemataceae | Controls | 0.03 |
| Actinobacteria_Actinobacteria_Actinomycetales_Propionibacteriaceae | Controls | 0.01 |
| Bacteroidetes_Bacteroidia_Bacteroidales_Bacteroidales_incertae_sedis | Controls | 0.01 |
| Firmicutes_Erysipelotrichia_Erysipelotrichales_Erysipelotrichaceae | Controls | 0.005 |
| Firmicutes_Clostridia_Clostridiales_Lachnospiraceae | Controls | 1.27E−07 |

Figure 3A:
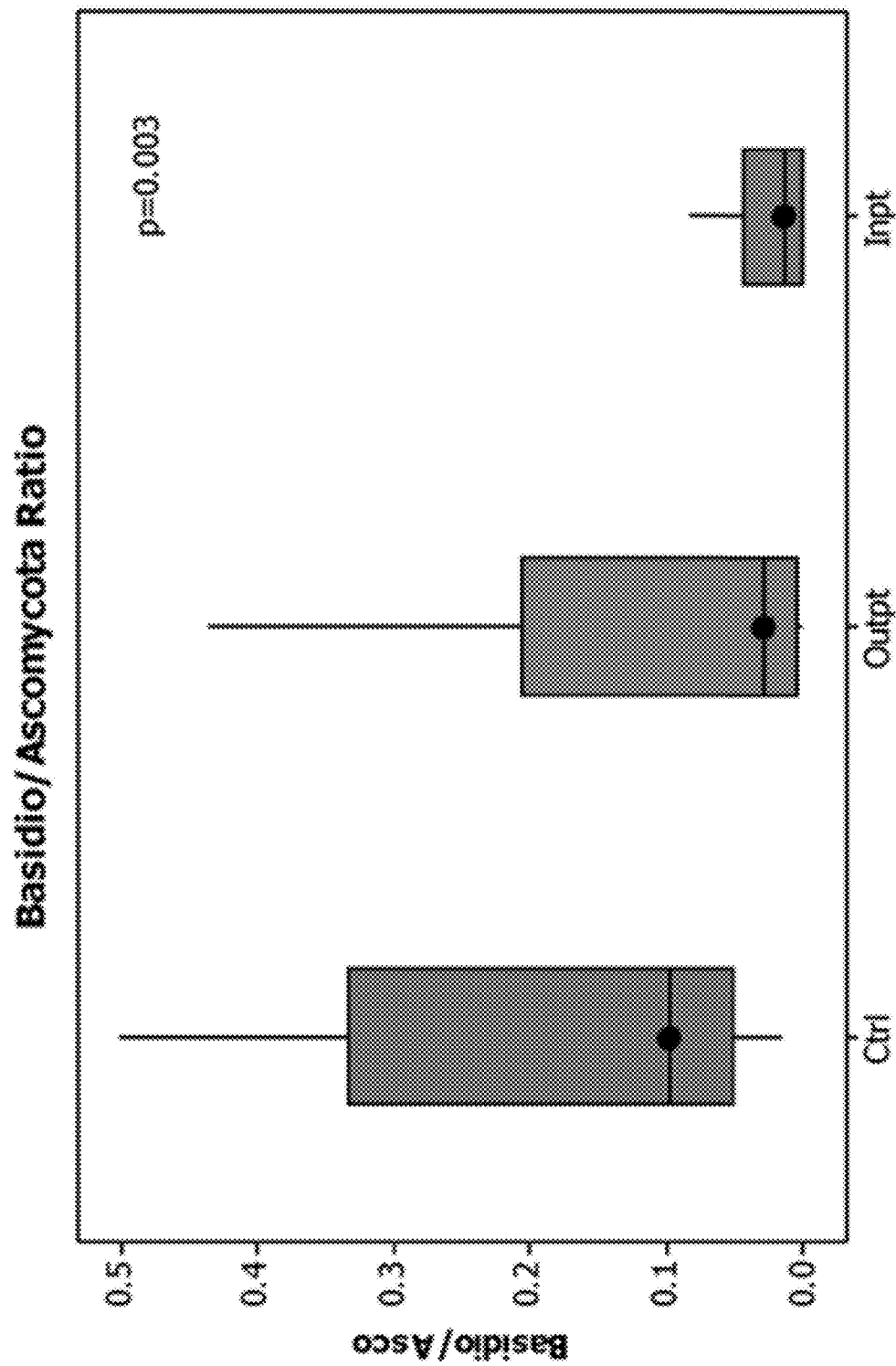
FIG. 3. Cross-sectional study of fungal taxa. (A) Significantly lower Basidiomycota/Ascomycota ratio in inpatients compared with outpatients and healthy controls. Data are presented as median and 95% CI with p-values based on Kruskal-Wallis test. Ctrl, controls; Inpt, inpatients with cirrhosis; Outpt, outpatients with cirrhosis. (B) Significantly lower Basidiomycota/Ascomycota ratio in inpatients with culture-positive infections compared with culture-negative, uninfected and healthy controls. Data are presented as median and 95% CI with p-values based on Kruskal-Wallis test. Cneg, culture-negative infections; Cpos, culture-positive infections; Ctrl, controls; Uninf, uninfected inpatients with cirrhosis. (C) Basidiomycota/Ascomycota ratio was low and statistically similar between outpatients on antibiotics and inpatient groups, compared with outpatients not on antibiotics and healthy controls. Data are presented as median and 95% CI with p-values based on Kruskal-Wallis test. Ctrl, controls; Inp-Inf, infected inpatients with cirrhosis; Inp-Uninf, uninfected inpatients with cirrhosis; OutAb, outpatients with cirrhosis on rifaximin and/or SBP prophylaxis; OutNAb, outpatients with cirrhosis not on rifaximin or SBP prophylaxis.
Figure 3B:
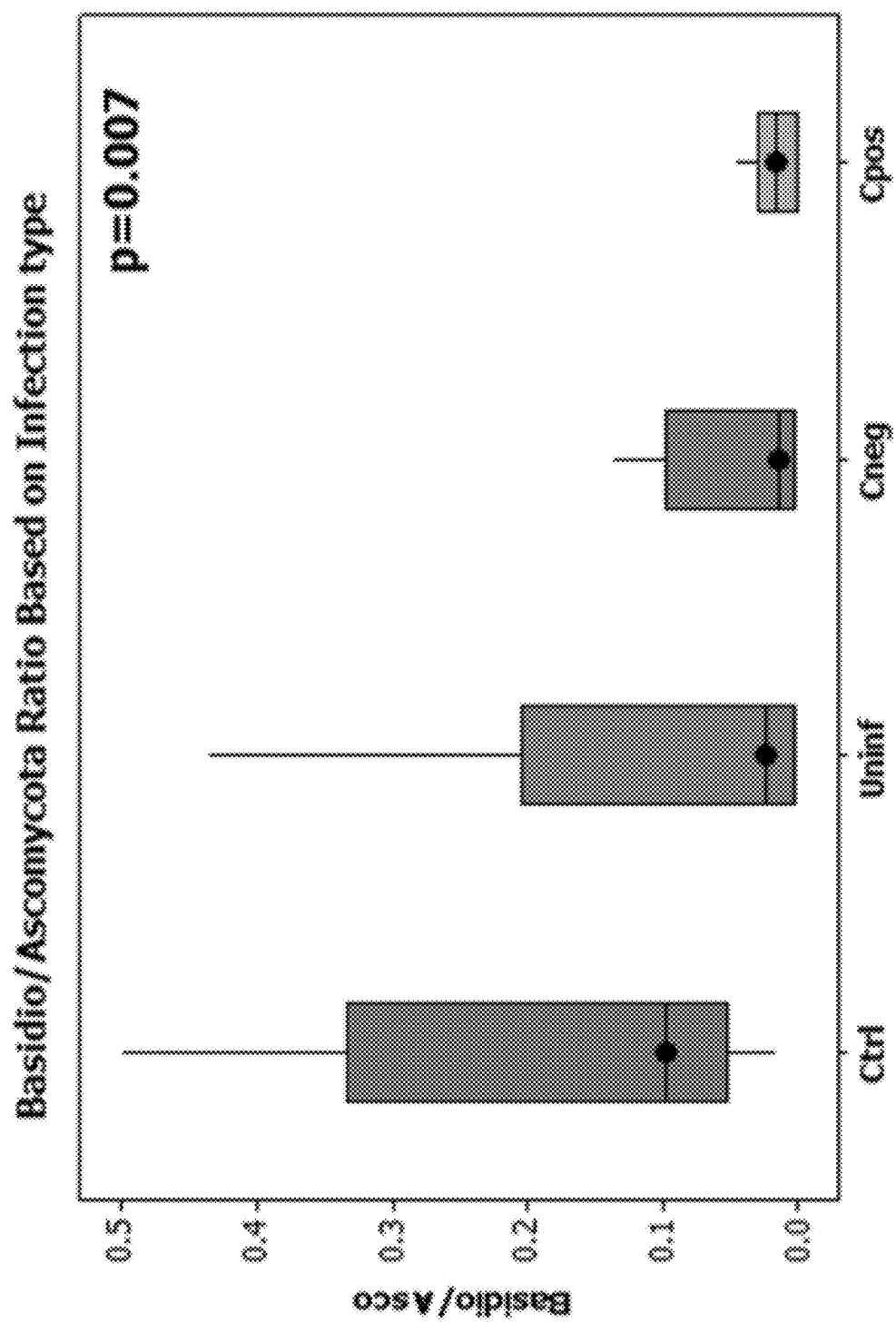
Figure 3C:
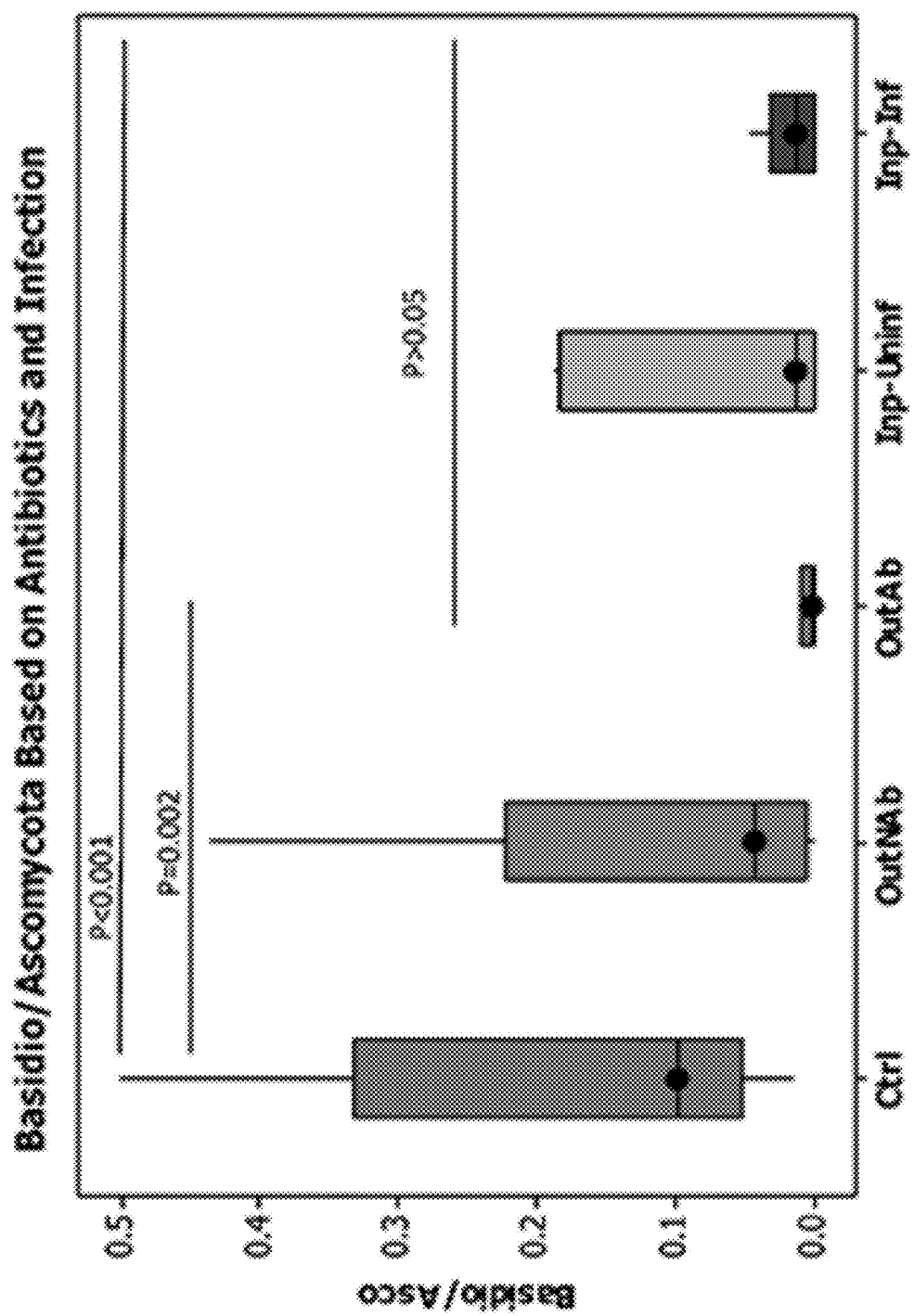
Figure 4A:
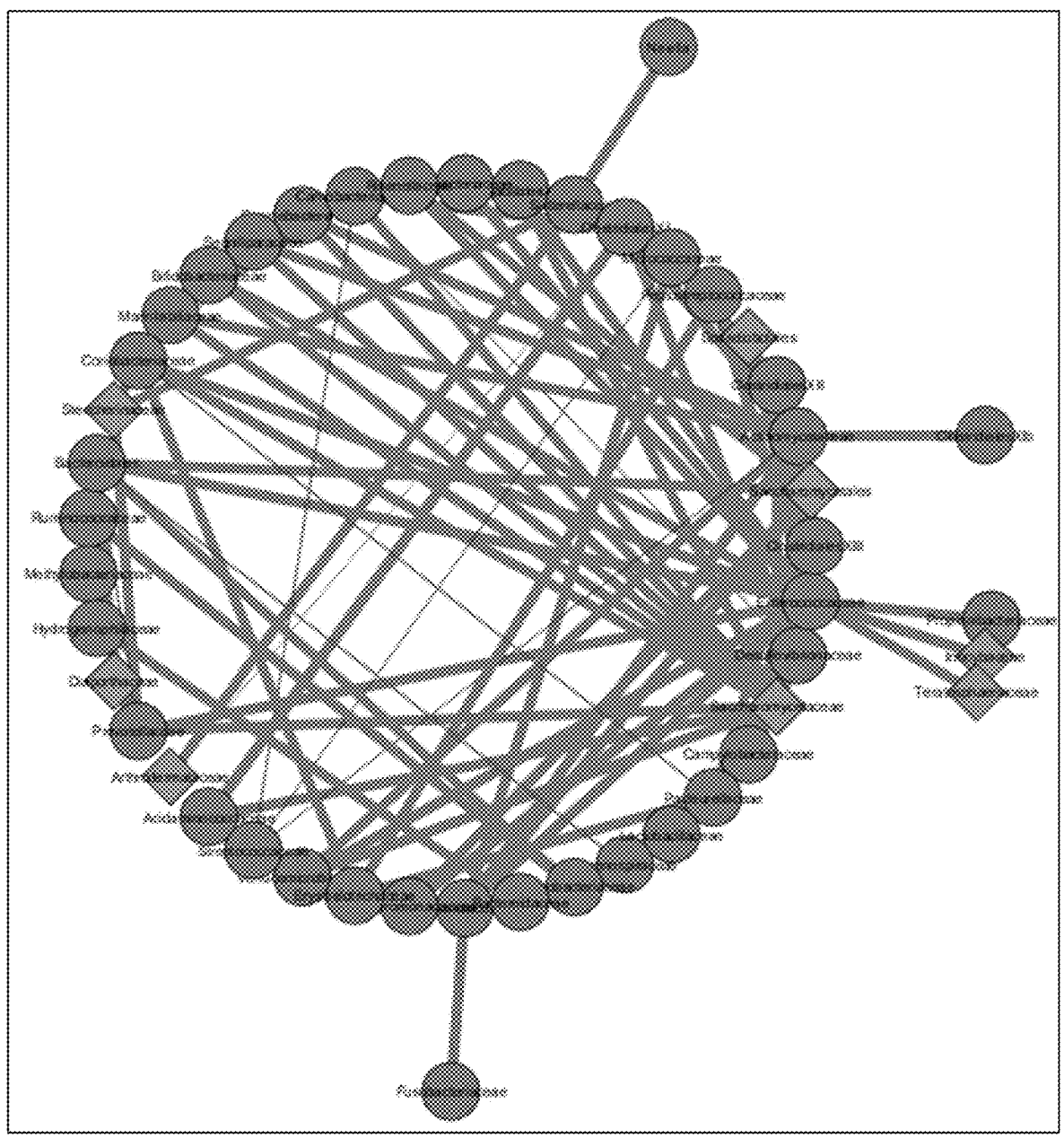
FIG. 4. Correlation networks between fungi and bacteria. (A) Correlation network demonstrates a dense linkage between bacteria (red nodes) and fungi (green nodes) with negative (red lines) and positive linkages (blue lines) in healthy controls. (B) Similar to healthy controls, correlation network in outpatient cirrhotics demonstrates a dense linkage between bacteria (red nodes) and fungi (green nodes) with negative (red lines) and positive linkages (blue lines). (C) Lower complexity in uninfected inpatient cirrhotics is seen between bacteria (red nodes) and fungi (green nodes) with negative (red lines) and positive linkages (blue lines). (D) Very low complexity in culture-negative infected inpatient cirrhotics is seen between bacteria (red nodes) and fungi (green nodes) with negative (red lines) and positive linkages (blue lines). (E) The lowest complexity in culture-positive infected inpatient cirrhotics is seen between bacteria (red nodes) and fungi (green nodes) with negative (red lines) and positive linkages (blue lines).
Figure 4B:
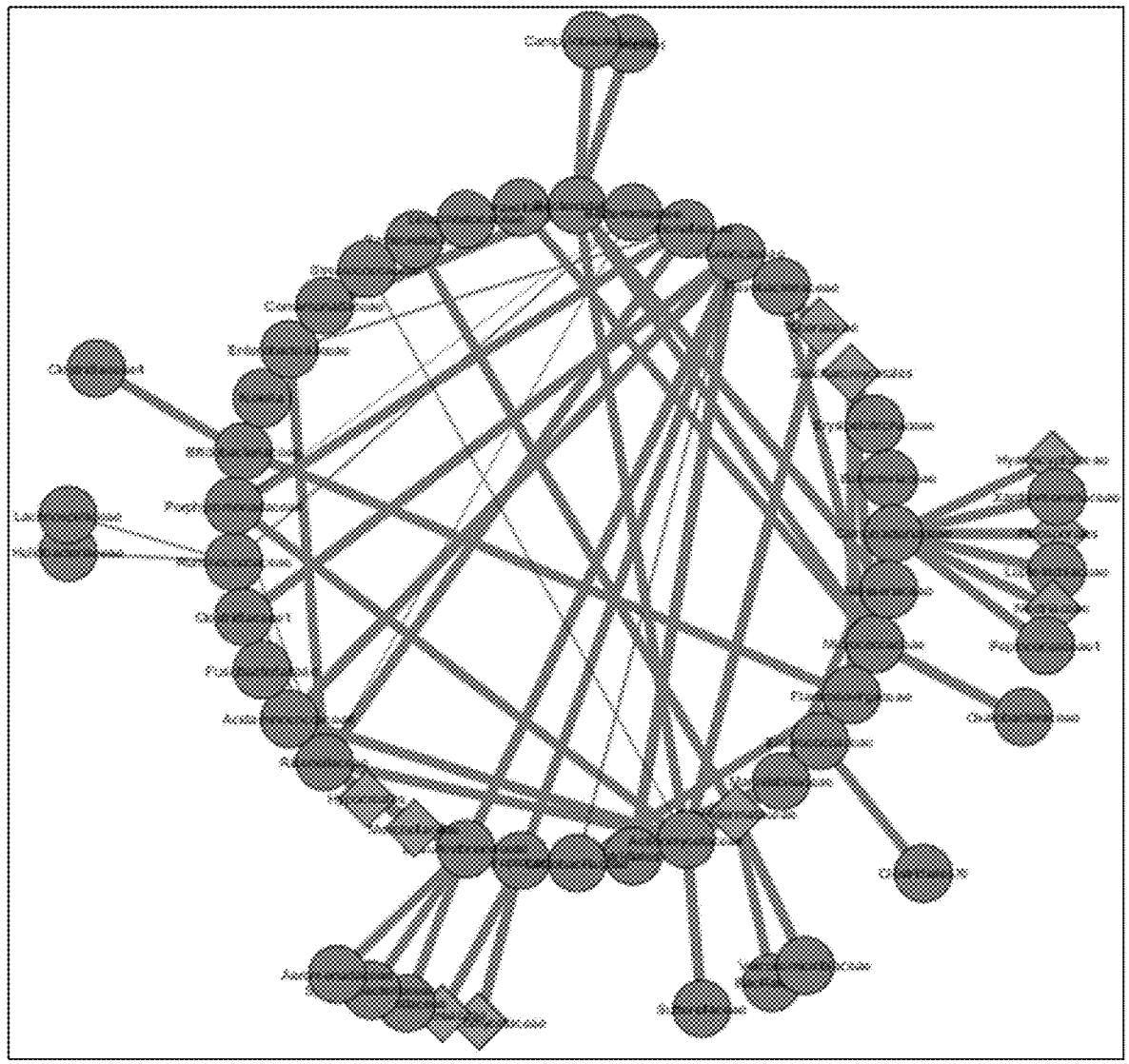
Figure 4C:
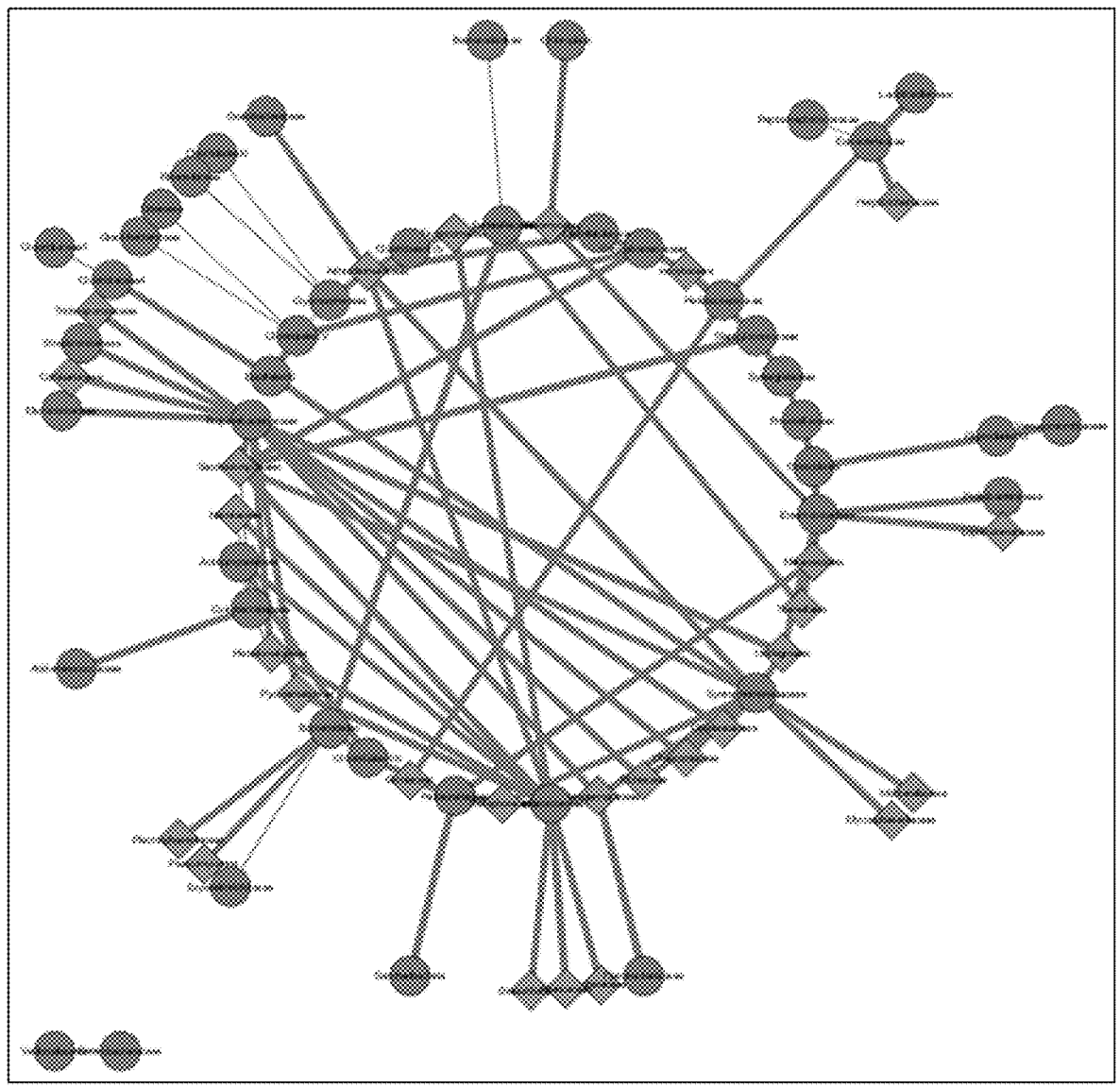
Figure 4D:
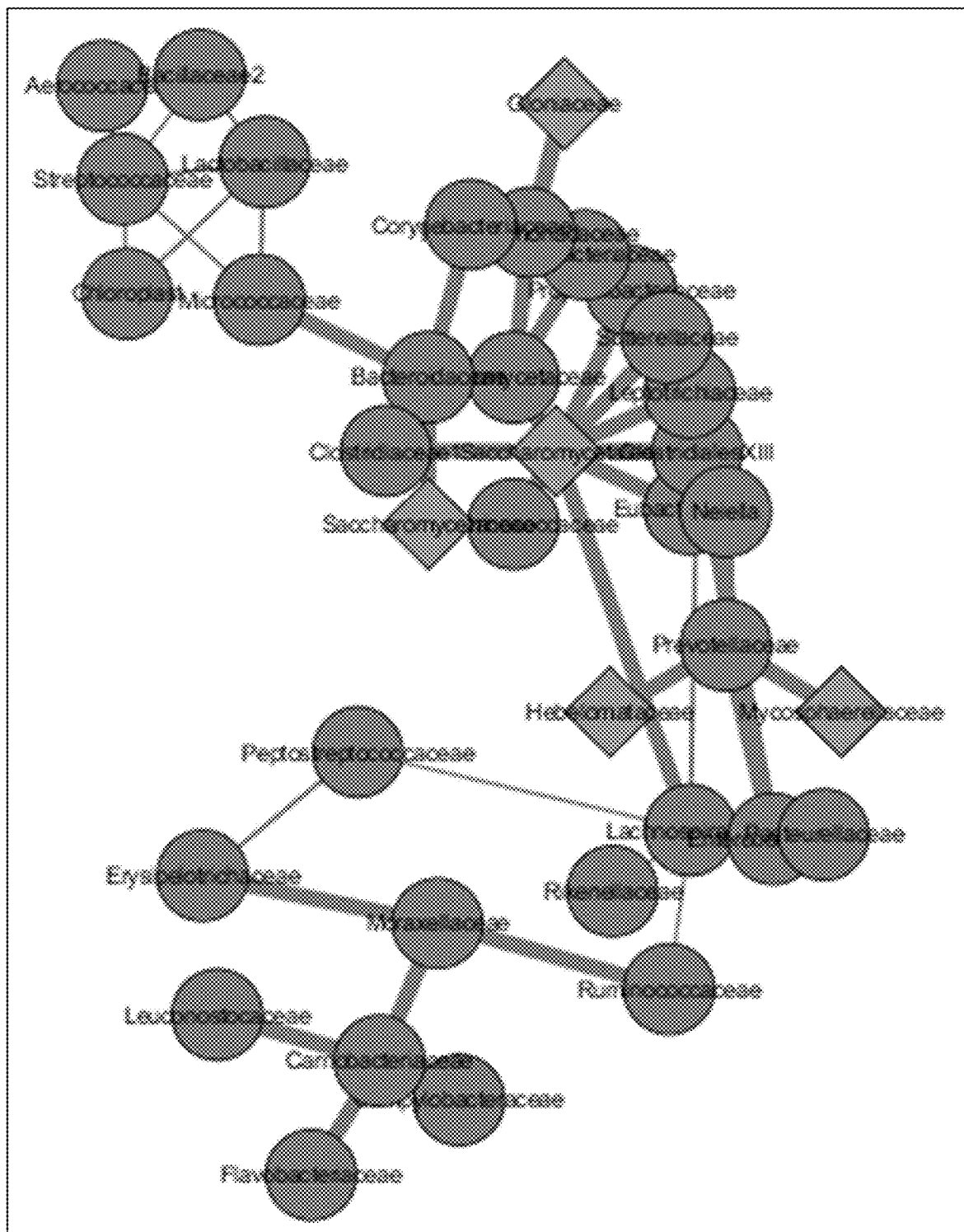
Figure 4E:
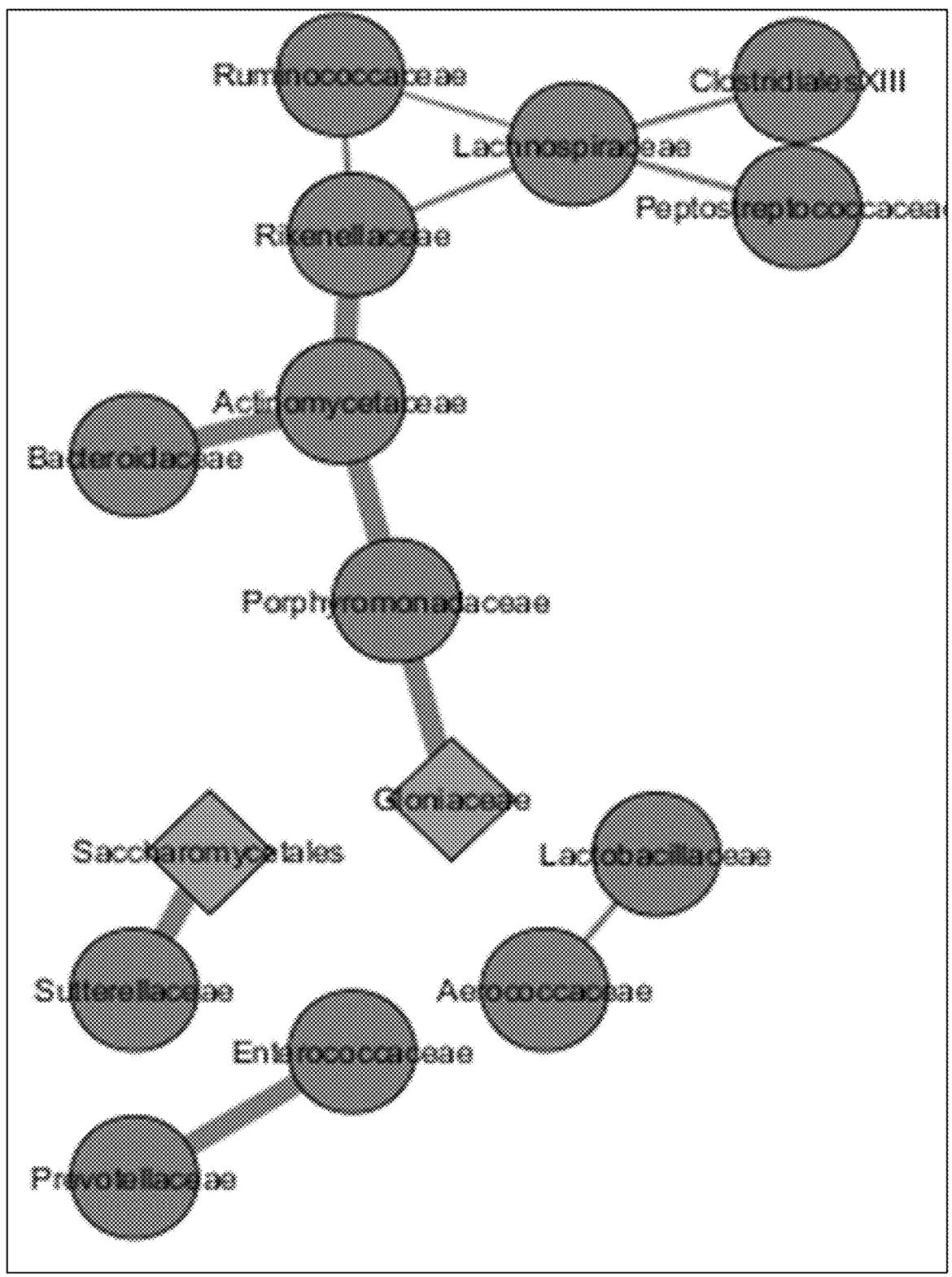

Fungal Phyla and Basidiomycota/Ascomycota Changes with Cirrhosis Severity and Groups This ratio has been used to define the fungal dysbiosis, and in the cross-sectional analysis, there was a significant reduction of this ratio in inpatients and lowest in culture-positive infections compared with the other groups (FIG. 3A,B). When this was studied with respect to infections and antibiotic use, the lowest was in the outpatients on antibiotics and in infected inpatients (FIG. 3C).

Correlations Between Bacteria and Fungi were Skewed in Infected Patients with Cirrhosis There were rich correlations between fungi and bacteria in healthy controls and outpatients with cirrhosis. This complexity reduced in inpatients without infections and culture-negative infections and was the lowest and most skewed in the patients with culture-positive infections (FIG. 4A-E).

The Novel Bacteroidetes/Ascomycota Ratio was Able to Predict 90-Day Hospitalizations Of the 143 patients, 90-day data were available for 123 patients because 12 died without getting readmitted and eight were lost to follow-up. Of these 123, 27 patients were admitted a median of 39 (IQR 14-71 days) post-enrolment. All patients were admitted for liver-related reasons (hepatic encephalopathy (HE) n=14, infections n=6, anasarca n=4, hyponatraemia n=3, gastrointestinal (GI) bleeding n=2), of which four patients had multiple reasons related to HE, infections and GI bleeding. Inpatient status, infection, endotoxin levels, HE and specific microbial phyla were different at enrolment between those who were admitted compared with the rest (Table 2). On univariate analysis, inpatient status, infection, HE, relative abundance of Bacteroidetes, Proteobacteria and Ascomycota had p<0.10. On multivariable analysis, HE (OR 3.5, CI 1.14 to 10.8, p=0.02) and Ascomycota relative abundance (OR 2.6, CI 1.02 to 8.8, p=0.04) were predictive, while Bacteroidetes relative abundance was associated with lower hospitalizations (OR 0.16, CI 0.02 to 0.98, p=0.05). We then calculated a Bacteroidetes/Ascomycota ratio, which then was again protective against 90-day hospitalizations (OR 0.10, CI 0.01 to 0.94, p=0.04) independent of HE (OR 5.3, CI 1.34 to 20.6, p=0.01). On Kruskal-Wallis, this median ratio was significantly lower in those who were hospitalized compared with those who remained free of hospitalizations (0.01 IQR 0.39 vs 0.47 IQR 0.54).

TABLE 2

Characteristics of patients who were admitted within 90 days

|  | Not readmitted (n = 96) | Readmitted (n = 27) |
|---|---|---|
| Clinical parameters |  |  |
| Age (years) | 57.9 ± 7.4 | 55.2 ± 7.5 |
| Gender (men/women) | 81/15 | 14/13* |
| Aetiology (HCV, alcohol, HCV + alcohol, NAFLD, others) | 38/10/15/21/12 | 7/7/4/4/3 |
| MELD score | 15.3 ± 6.9 | 17.5 ± 8.1 |
| Prior hepatic encephalopathy | 35 | 14* |
| Lactulose alone/any rifaximin | 15/20 | 11/3* |
| SBP prophylaxis | 10 | 3 |
| Proton pump inhibitors | 46 | 14 |
| Non-selective beta-blockers | 39 | 10 |
| Diabetes | 26 | 8 |
| Infection | 23 | 15* |
| Inpatient group | 34 | 17* |
| Microbiota parameters |  |  |
| Fungal Shannon index | 1.0 ± 0.7 | 0.71 ± 0.4* |
| All Ascomycota (median relative abundance) | 76% | 98%* |
| All Basidiomycota (median relative abundance) | 0% | 0.1% |
| Basidiomycota/Ascomycota ratio | 0.3 ± 0.8 | 0.06 ± 0.10* |
| Bacterial Shannon index | 1.4 ± 0.4 | 1.3 ± 0.6 |
| All Proteobacteria (median relative abundance) | 2% | 7%* |
| All Bacteroidetes (median relative abundance) | 40% | 8%* |
| All Firmicutes (median relative abundance) | 39% | 45% |

MELD, model for end-stage liver disease;
NAFLD, non-alcoholic fatty liver disease;
SBP, spontaneous bacterial peritonitis.

Prospective Studies

Natural History Study

There was no change in MELD score (8.8±2.9 vs 9.1±3.1, p=0.39), development of HE or other complications, or hospitalizations between the visits which were 6±1 months apart (Table 3). On linear discriminant analysis effect size (LEFSe), there were no changes in individual bacterial or fungal taxa. This was also reflected in stable bacterial (visit-1, 1.54±0.40 vs visit-2, 1.43±0.37, p=0.38) or fungal (visit-1, 1.07±0.56 vs visit-2 1.31±0.56, p=0.11) diversity.

TABLE 3

Demographics and characteristics of subjects in the three longitudinal studies

|  | Natural history | Pre-PPI/post-PPI baseline† | | Preantibiotics/postantibiotics‡ (n = 7) | |
| --- | --- | --- | --- | --- | --- |
|  | baseline* (n = 15) | Cirrhosis (n = 13) | Controls (n = 10) | Antibiotics (n = 7) | No antibiotics (n = 7) |
| Age (years) | 55.2 ± 5.9 | 54.2 ± 4.7 | 52.1 ± 9.5 | 64.3 ± 5.2 | 61.7 ± 11.5 |
| Gender (men/women) | 8/7 | 10/3 | 8/2 | 7/0 | 7/0 |
| Aetiology of cirrhosis (HCV, alcohol, HCV + alcohol, NAFLD, other) | 3/5/0/7/0 | 5/2/1/3/2 | — | 4/2/1/0 | 5/2/0 |
| MELD score | 8.8 ± 2.9 | 18.1 ± 2.7 | — | 13.2 ± 2.5 | 12.1 ± 2.5 |
| Prior hepatic encephalopathy | 4 | 0 | — | 7 | 7 |
| Lactulose/any rifaximin | 4/0 | 0/0 | — | 0/7 | 0/7 |
| Proton pump inhibitors | 5 | 0 at baseline | 0 at baseline | 6 | 6 |
| Non-selective beta-blockers | 4 | 4 | 0 | 5 | 5 |
| Diabetes | 5 | 2 | — | 4 | 5 |

*These subjects were followed over 6 months without any change in cirrhosis natural history; the table demonstrates baseline values.
†Subjects tested before and after 14 days of 40 mg omeprazole daily; column values reflect baseline values.
‡Outpatients with recurrent HE were randomised into receiving antibiotics for 5 days or not; these are the baseline values.
MELD, model for end-stage liver disease;
NAFLD, non-alcoholic fatty liver disease.

Pre-PPI/Post-PPI Use

All subjects were able to tolerate the omeprazole therapy as reported (Bajaj J S, et al. Am J Physiol Gastrointest Liver Physiol 2014 307:G951-G957). There was no change in MELD score (8.1±2.7 vs 7.9±3.5, p=0.41) or new complications in the patients with cirrhosis during the trial (Table 3). There were no changes in fungal taxa on LEFSe but as previously reported a significant change in bacteria reflecting oral microbial presence in the stool postomeprazole was seen (Table 11) (Bajaj J S, et al. Am J Physiol Gastrointest Liver Physiol 2014 307:G951-G957; Imhann F, et al. Gut 2016 65:740-8). This was accompanied by a reduction in bacterial diversity in both controls (pre 1.88±0.16 vs post 1.63±0.22, p=0.004) and patients with cirrhosis (pre 1.89±0.25 vs post 1.54±0.34, p=0.05), while fungal diversity remained statistically unchanged in both groups (control pre1.92±0.48 vs post 1.73±0.61, p=0.46; cirrhosis pre 1.64±0.34 vs post 1.45±0.38, p=0.39).

TABLE 11

LEFSe findings pre/post PPI therapy

| Comparison | Phylum_Order_Family_Genus | Group with higher LDA | P value |
| --- | --- | --- | --- |
| Cirrhosis pre vs post | Firmicutes_Bacilli_Lactobacillales_Streptococcaceae | Cirrhosis Post | 0.0001 |
|  | Proteobacteria_Gammaproteobacteria_Pasteurellales_Pasteurellaceae | Cirrhosis Post | 0.018 |
|  | Actinobacteria_Actinobacteria_Bifidobacteriales_Bifidobacteriaceae | Cirrhosis Pre | 0.03 |
| Control pre vs post | Firmicutes_Bacilli_Lactobacillales_Streptococcaceae | Cirrhosis Post | 0.0008 |
|  | Firmicutes_Negativicutes_Selenomonadales_Acidaminococcaceae | Cirrhosis Pre | 0.04 |
|  | Bacteroidetes_Bacteroidia_Bacteroidales_Bacteroidaceae | Cirrhosis Pre | 0.03 |
| Cirrhosis post vs Control post | Firmicutes_Clostridia_Clostridiales_Syntrophomonadaceae | Cirrhosis Post | 0.02 |
|  | Firmicutes_Clostridia_Clostridiales_Lachnospiraceae | Cirrhosis Post | 0.01 |
|  | Firmicutes_Clostridia_Clostridiales_Eubacteriaceae | Cirrhosis Post | 0.04 |
|  | Actinobacteria_Actinobacteria_Bifidobacteriales_Bifidobacteriaceae | Cirrhosis Post | 0.02 |
|  | Firmicutes_Bacilli_Lactobacillales_Carnobacteriaceae | Cirrhosis Post | 0.01 |
|  | Verrucomicrobia_Verrucomicrobiae_Verrucomicrobiales_Verrucomicrobiaceae | Cirrhosis Post | 0.04 |

TABLE 11-continued

LEFSe findings pre/post PPI therapy

| Comparison | Phylum_Order_Family_Genus | Group with higher LDA | P value |
|---|---|---|---|
| | Firmicutes_Erysipelotrichia_Erysipelotrichales_Erysipelotrichaceae | Cirrhosis Post | 0.03 |

Preantibiotics/Postantibiotics

Fourteen cirrhotics with hepatic encephalopathy controlled on lactulose and rifaximin were included; seven were administered the antibiotics, while the remaining were observed without it. No signs of infection were noted and the groups were balanced with respect to cirrhosis severity (Table 3).

Fungal and Bacterial Diversity Reduced and Taxa Changed after Antibiotic Use

Figure 5A:
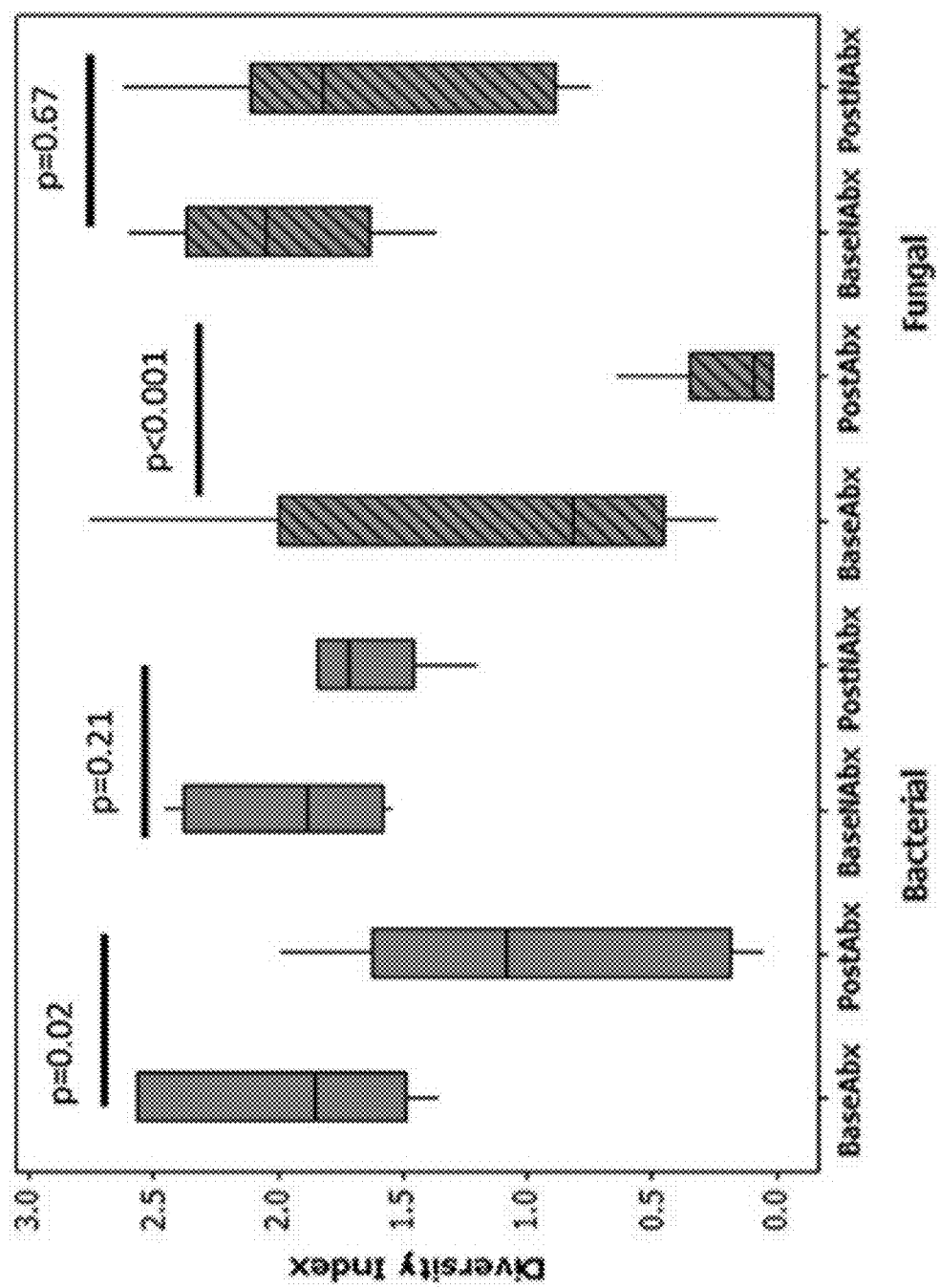
FIG. 5. Pre-outpatient and post-outpatient antibiotics. (A) Shannon diversity indices for both fungi and bacteria were the lowest in patients with cirrhosis who received antibiotics compared with their baseline and both time periods of the no-antibiotics group. Data are presented as median and 95% CI with p-values based on Kruskal-Wallis test. Abx, antibiotics; Base, baseline; NAbx, no antibiotics; Post, after 5 days. (B) Specific changes in bacterial and fungal relative abundance after day 5 (green bars) compared with preantibiotic baseline (red bars) in the cirrhotic group receiving antibiotics using linear discriminant analysis effect size (LEFSe). (C) Cladogram showing a comparison at day 5 of the cirrhotics who received antibiotics (red) compared with those who did not (green) using LEFSe.
Figure 5B:
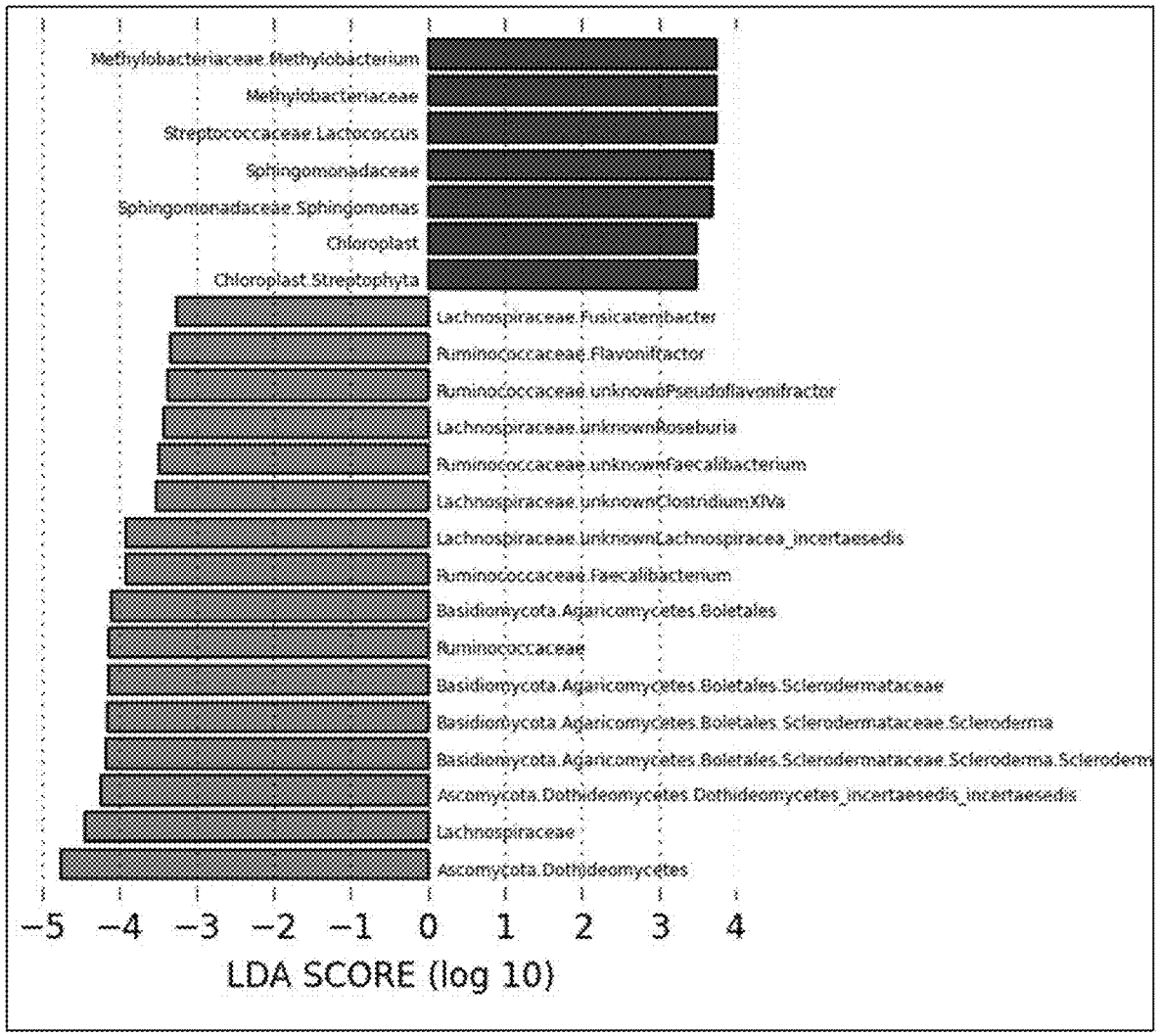
Figure 5C:
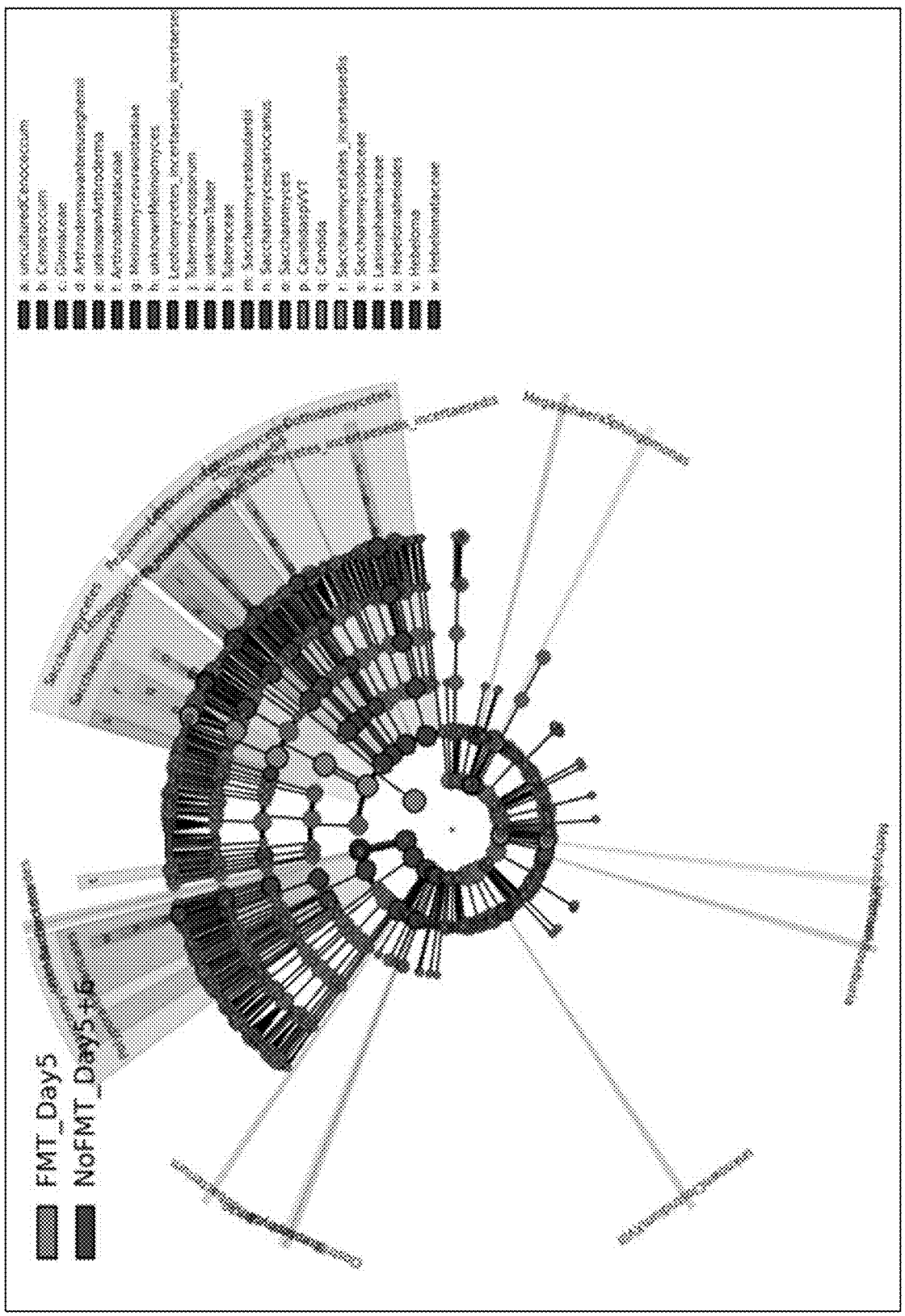

Diversity of fungi and bacteria was statistically similar between groups at baseline but significantly reduced after antibiotic therapy (FIG. 5A, Table 3). The Shannon diversity index remained statistically similar in those not administered antibiotics. Specifically on LEFSe, those given antibiotics had a significantly lower relative abundance of autochthonous bacterial taxa and of certain fungi compared with their baseline (FIG. 5B). In patients with cirrhosis who were not administered antibiotics, there were comparatively minimal changes in bacterial and fungal taxa between baseline and day 5. Compared with baseline, the antibiotics groups had a significant decrease in the relative abundance of autochthonous bacterial taxa and decrease in fungal taxa belonging to Sclerodermataceae and Dothideomycetes (FIG. 5C). After antibiotics, these fungi were not found and there was an increase in the relative abundance of taxa belonging to Chloroplast, Methylobacterium and Streptococcaceae. No significant LEFSe changes between baseline and day 5 of the no-antibiotic group were identified. At day 5 compared with the no-antibiotics group, there was a significant increase in the relative abundance of Candida in the antibiotics group, while other fungal taxa significantly decreased including Saccharomyces boulardii. The antibiotic group also had a significantly lower relative abundance of Bifidobacterium and Roseburia and higher relative abundance of Chloroplast and Methylobacterium (FIG. 5C).

Discussion

With the increasing prevalence of infections as a cause of organ failure and death in cirrhosis, there is a need to develop appropriate means to define their evolving microbiology (Bajaj J S, et al. Hepatology 2012 56:2328-35; Bonnel A R, et al. Clin Gastroenterol Hepatol 2011 9:727-38). The study defines the important role of the gut mycobiome in outpatients and inpatients with cirrhosis and their evolving role in the prediction of future hospitalizations.

This study spanned the entire spectrum of cirrhosis from compensated outpatients through patients who were hospitalized with and without infections. The results point towards a correlation between diversity in the fungal and bacterial taxa with worsening of the diversity with more advanced stages of disease. Specific bacterial phyla, such as Proteobacteria, increase with worsening cirrhosis, while the worsening MELD score was correlated negatively in the Basidiomycota/Ascomycota ratio.

On individual taxa analysis using LEFSe, this diversity was represented by a greater relative abundance of fungal taxa and autochthonous bacteria and lower Candida and potentially pathogenic bacteria such as Enterococcaceae in controls compared with inpatients or outpatients with cirrhosis. Similarly, autochthonous bacterial taxa and a greater variety of fungi spanning all phyla were seen in outpatients compared with a greater relative abundance of Candida and potentially pathogenic bacterial taxa in inpatients.

Within outpatients, the lowest bacterial and fungal diversity was found in those on antibiotics, which was also seen when broad-spectrum antibiotics were administered longitudinally. This bacterial diversity collapse with antibiotics cross-sectionally and longitudinally was accompanied by an increase in relative abundance of Ascomycota components such as Candida. These findings in the longitudinal cohort are even more striking given that these were patients already on rifaximin and lactulose. Despite this skewed gut milieu, broad-spectrum antibiotics were able to further disrupt the bacterial and fungal population, indicating the pervasive, additive impact of antibiotics that are used rampantly and commonly in this group.

Antibiotics are one of the major risk factors for emergence of fungi (Bajaj J S, et al. Hepatology 2012 56:2328-35; Lahmer T, et al. Mycopathologia 2015 179:63-71), which in this study was evaluated comparing uninfected patients with those with culture-negative and culture-positive infections and outpatients on antibiotics (Pérez-Cobas A E, et al. Gut 2013 62:1591-601). While infected and uninfected inpatients were similar on MELD score and diversity as a whole, patients with culture-positive infections demonstrated a lower diversity, lower Basidiomycota/Ascomycota and relative abundance of fungi on LEFSe compared with patients with culture-negative infections. This diversity was also lower than in antibiotic-using outpatients. These findings point towards an inherent gut milieu in patients with culture-positive infections, a proportion of which had Candida infections, which is independent of antibiotics and MELD score and could be a target of modulation with strategies other than further antibiotic therapy.

Interestingly, as opposed to antibiotic therapy, PPI therapy did not significantly affect fungal diversity in controls or cirrhotics, in contrast to bacterial diversity. While the mechanism is not clear, it could be due to the reduction in total bacterial abundance seen with antibiotics, which is not usually seen with PPIs (Panda S, et al. PLoS One 2014 9:e95476). Being saprophytic, fungi are dependent on bacteria for nutrition, and it is possible that substitution of the usual faecal microbiota with oral microbiota in the case of PPI use could still maintain their food source while a significant reduction in the entire population abundance, as occurs with antibiotic use could secondarily impact fungi. This nuanced interaction is also represented by the lack of correlation between fungal diversity and endotoxin and between fungal phyla and MELD directly. Therefore, fungal presence is not increased directly by the usual gram-negative bacterial taxa increase that accompanies advancing cirrhosis but could be modulated by other factors. Moreover, the complex correlations between fungi and bacteria that existed in uninfected inpatients, outpatients and controls were reduced to a skewed linkage pattern in infected patients, both culture-positive and culture-negative. This was similar to patterns seen in inflammatory bowel disease, although no significant alterations in *Saccharomyces cerevisiae* were observed, lending the findings specificity for cirrhosis (Sokol H, et al. Gut 2016 gutjnl-2015-310746). Interactions between these two kingdoms is complex due to multiple nutritional, quorum-sensing and competitive interactions (Peay K G, et al. Nat Rev Microbiol 2016 14:434-47; Wang Z K, et al. Aliment Pharmacol Ther 2014 39:751-66) and based on this study, is differentially affected by antibiotics, acid suppression or cirrhosis severity.

Interestingly, there were no changes in the bacterial or fungal diversity or in composition on LEFSe in outpatients with cirrhosis followed either short-term (advanced group randomised to no-antibiotics) or long-term (on 6-month follow-up). This extends prior studies of bacterial diversity into the fungal realm and demonstrates the underlying resilience of this composition, provided the underlying cirrhosis course is stable (Bajaj J S, et al. J Hepatol 2014 60:940-7). The resilience was also reflected by the non-significant impact of diabetes, whose effect may have been diluted by the already skewed microbiota in cirrhosis, as previously shown (Forslund K, et al. Nature 2015 528:262-6; Bajaj J S, et al. Sci Rep 2015 5:18559).

The current clinical practice for treating signs and symptoms suggestive of infections (high WBC count, SIRS criteria, hepatic encephalopathy) in patients with cirrhosis even without an identifiable micro-organism is to initiate antibiotics to treat a presumed bacterial source (Malik R, et al. J Hepatol 2009 51:426-9). The current results demonstrate a reduction in fungal diversity with overabundance of Ascomycota in culture-negative and even in bacterial culture-positive infections. The most common fungal infections in cirrhosis, peritonitis, fungaemia and esophagitis are usually due to Ascomycota members and have a presumed gut origin (Bajaj J S, et al. Hepatology 2012 56:2328-35; Lahmer T, et al. Mycopathologia 2015 179:63-71; Wang Z K, et al. Aliment Pharmacol Ther 2014 39:751-66). These infections, when clinically confirmed using current culture techniques, carry a devastating prognosis (Alexopoulou A, et al. J Hepatol 2015 63:1043-5). A dysbiotic mycobiome is characterized by an altered Basidiomycota/Ascomycota and higher Ascomycota, which was indeed also observed in advanced and infected cirrhosis could be exacerbated by this rampant antibiotic use (Lahmer T, et al. Mycopathologia 2015 179:63-71; Alexopoulou A, et al. J Hepatol 2015 63:1043-5). Results also show that this higher relative abundance of Ascomycota could also predict hospitalizations within 90 days independent of bacterial components of the microbiome and clinical biomarkers. This was in contrast to the potentially protective role of Bacteroidetes that replicates prior experience (Bajaj J S, et al. Sci Rep 2015 5:18559). Interestingly, the ratio of Bacteroidetes/Ascomycota rather than Basidiomycota/Ascomycota was predictive of hospitalizations, underlining the finding that both mycobiome and bacterial microbiome needs to be taken into consideration to potentially improve prognostication.

Cumulatively, these results demonstrate that there are systematic reductions in fungal diversity which parallel bacterial diversity in outpatients and inpatients with cirrhosis. This dysbiosis changes differentially with antibiotics and PPI use, but is otherwise stable over time. A combined bacterial-fungal dysbiosis metric, Bacteroidetes/Ascomycota, can independently predict 90-day hospitalizations in patients with cirrhosis. These findings demonstrate that fungi are major modulators of the overall gut microbial dysbiosis in cirrhosis and further studies to determine if reducing the relative abundance of Ascomycota can prevent hospitalizations or development of fungal infections are needed.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with liver cirrhosis, comprising
   a) assaying a gastrointestinal bacterial sample from the subject for bacterial taxa to generate a bacterial profile;
   b) comparing the bacterial profile to control profiles to predict fungal dysbiosis; and
   c) treating the subject for fungal dysbiosis,
   wherein the bacterial profile associated with fungal dysbiosis comprises a reduction in bacterial diversity.

2. The method of claim 1, wherein the sample is culture-negative for fungal infection.

3. The method of claim 1, wherein the sample comprises DNA from a stool, rectal swab or mucosal biopsy.

4. The method of claim 3, wherein assaying the sample comprises PCR amplification of the DNA with bacterial specific primers for variable regions of the 16S rRNA gene.

5. The method of claim 1, wherein the fungal dysbiosis is an indication of fungal overgrowth, wherein the subject is treated with anti-fungal therapy.

6. The method of claim 1, wherein the fungal dysbiosis is an indication of excessive antibiotic use, wherein the subject is treated by ceasing or reducing antibiotic therapy.

7. The method of claim 1, wherein the fungal dysbiosis is an indication of microbiome depletion, wherein the subject is treated with probiotics, prebiotics, or fecal microbial transplant.

8. The method of claim 1, wherein the bacteria taxa are selected from the group consisting of Collinsella, *Enterococcus, Streptococcus, Coprococcus, Fusicatenibacter, Lachnospiraceae* incertae sedis, *Roseburia, Ruminococcus2, Anaerostipes, Lachnobacterium, Robinsoniella, Ruminococcus, Anaerotruncus, Hydrogenoanaerobacterium*, and *Megasphaera*.

* * * * *